(12) United States Patent
Ouderkirk et al.

(10) Patent No.: US 11,665,969 B2
(45) Date of Patent: May 30, 2023

(54) NANOVOIDED ELECTROACTIVE POLYMER DEVICES, SYSTEMS, AND METHODS

(71) Applicant: Meta Platforms Technologies, LLC, Menlo Park, CA (US)

(72) Inventors: Andrew John Ouderkirk, Redmond, WA (US); Katherine Marie Smyth, Seattle, WA (US); Eric C. Schmitt, Boston, MA (US); Nagi H. Elabbasi, Framingham, MA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 1094 days.

(21) Appl. No.: 16/041,858

(22) Filed: Jul. 23, 2018

(65) Prior Publication Data
US 2019/0296218 A1    Sep. 26, 2019

Related U.S. Application Data

(60) Provisional application No. 62/646,900, filed on Mar. 22, 2018, provisional application No. 62/650,254, filed on Mar. 29, 2018.

(51) Int. Cl.
*H01L 41/193* (2006.01)
*H01L 41/047* (2006.01)
(Continued)

(52) U.S. Cl.
CPC .......... *H01L 41/193* (2013.01); *A61B 3/0008* (2013.01); *A61B 3/0033* (2013.01);
(Continued)

(58) Field of Classification Search
CPC ......... H01L 41/09; H01L 41/29; H01L 41/45; H01L 41/047; H01L 41/083;
(Continued)

(56) References Cited

U.S. PATENT DOCUMENTS 60,109 A    11/1866  Woodward
3,571,555 A   3/1971  Townes et al.
(Continued)

FOREIGN PATENT DOCUMENTS

KR    10-2011-0107812 A    10/2011
KR        101675093 B1     11/2016
(Continued)

OTHER PUBLICATIONS

Cao et al., Grain Size and Domain Size Relations in Bulk Ceramic Ferroelectric Materials, J. Phys. Chem Solids vol. 57, No. 10, pp. 1499-1505, 1996.
(Continued)

*Primary Examiner* — Shawki S Ismail
*Assistant Examiner* — Monica Mata
(74) *Attorney, Agent, or Firm* — Greenberg Traurig, LLP

(57) ABSTRACT

An electroactive device may include (1) an electroactive polymer element having a first surface and a second surface opposite the first surface, the electroactive polymer element comprising a nanovoided polymer material, (2) a primary electrode abutting the first surface of the electroactive polymer element, and (3) a secondary electrode abutting the second surface of the electroactive polymer element. The electroactive polymer element may be deformable from an initial state to a deformed state by application of an electrostatic field produced by a potential difference between the primary electrode and the secondary electrode. Various other devices, systems, and methods are also disclosed.

19 Claims, 18 Drawing Sheets

(51) Int. Cl.

| | | |
|---|---|---|
| *H01L 41/09* | (2006.01) | |
| *H01L 41/29* | (2013.01) | |
| *H01L 41/317* | (2013.01) | |
| *H01L 41/45* | (2013.01) | |
| *H01L 41/18* | (2006.01) | |
| *H01L 41/083* | (2006.01) | |
| *A61B 3/00* | (2006.01) | |
| *A61B 3/103* | (2006.01) | |
| *G02B 27/00* | (2006.01) | |
| *G02B 27/01* | (2006.01) | |
| *H01M 4/04* | (2006.01) | |
| *H01M 4/60* | (2006.01) | |
| *H01L 41/293* | (2013.01) | |
| *A61B 3/06* | (2006.01) | |

(52) U.S. Cl.
CPC ............ *A61B 3/0075* (2013.01); *A61B 3/103* (2013.01); *G02B 27/0025* (2013.01); *G02B 27/0172* (2013.01); *G02B 27/0176* (2013.01); *H01L 41/047* (2013.01); *H01L 41/0472* (2013.01); *H01L 41/083* (2013.01); *H01L 41/09* (2013.01); *H01L 41/092* (2013.01); *H01L 41/0986* (2013.01); *H01L 41/183* (2013.01); *H01L 41/29* (2013.01); *H01L 41/293* (2013.01); *H01L 41/317* (2013.01); *H01L 41/45* (2013.01); *H01M 4/0428* (2013.01); *H01M 4/602* (2013.01); *A61B 3/06* (2013.01); *G02B 2027/0178* (2013.01)

(58) Field of Classification Search
CPC ... H01L 41/092; H01L 41/183; H01L 41/193; H01L 41/293; H01L 41/317; H01L 41/0472; H01L 41/0986; A61B 3/06; A61B 3/0008; A61B 3/0033; A61B 3/0075; A61B 3/103; H01M 4/602; H01M 4/0428; G02B 27/0025; G02B 27/0172; G02B 27/0176; G02B 2027/0178
USPC ........................................................ 310/366
See application file for complete search history.

(56) References Cited

U.S. PATENT DOCUMENTS

| | | | |
|---|---|---|---|
| 3,797,922 | A | 3/1974 | Plummer |
| 4,477,158 | A | 10/1984 | Pollock et al. |
| 5,154,862 | A | 10/1992 | Reagan et al. |
| 5,225,244 | A | 7/1993 | Aharoni et al. |
| 5,663,779 | A | 9/1997 | Karasawa |
| 5,956,183 | A | 9/1999 | Epstein et al. |
| 6,081,388 | A | 6/2000 | Widl |
| 6,420,441 | B1 | 7/2002 | Allen et al. |
| 6,918,670 | B2 | 7/2005 | Blum et al. |
| 7,008,054 | B1 | 3/2006 | Kurtin et al. |
| 7,118,219 | B2 | 10/2006 | Itagaki |
| 7,125,508 | B2 | 10/2006 | Ide et al. |
| 7,864,440 | B2 | 1/2011 | Berge |
| 7,866,816 | B2 | 1/2011 | Kurtin |
| 8,210,678 | B1 | 7/2012 | Farwig |
| 8,441,737 | B2 | 5/2013 | Buch et al. |
| 9,292,085 | B2 | 3/2016 | Bennett et al. |
| 10,187,568 | B1 | 1/2019 | Tran et al. |
| 10,409,089 | B2 | 9/2019 | Pugh et al. |
| 10,698,224 | B1 | 6/2020 | Cooke et al. |
| 10,754,145 | B1 | 8/2020 | Ouderkirk et al. |
| 10,881,287 | B1 | 1/2021 | Ouderkirk et al. |
| 10,928,558 | B1 | 2/2021 | Cooke et al. |
| 10,928,656 | B1 | 2/2021 | Smyth et al. |
| 10,962,791 | B1 | 3/2021 | Ouderkirk et al. |
| 11,011,739 | B1 | 5/2021 | Ouderkirk et al. |
| 11,048,075 | B1 | 6/2021 | Ouderkirk et al. |
| 2003/0003295 | A1 | 1/2003 | Dreher et al. |
| 2003/0054115 | A1 | 3/2003 | Albano et al. |
| 2003/0067245 | A1 | 4/2003 | Pelrine et al. |
| 2003/0083433 | A1 | 5/2003 | James et al. |
| 2003/0128496 | A1 | 7/2003 | Allen et al. |
| 2004/0096672 | A1 | 5/2004 | Lukas et al. |
| 2006/0024976 | A1 | 2/2006 | Waldfried et al. |
| 2006/0073424 | A1 | 4/2006 | Koveshnikov et al. |
| 2006/0228092 | A1 | 10/2006 | Hebrink et al. |
| 2006/0247404 | A1 | 11/2006 | Todd |
| 2007/0035839 | A1 | 2/2007 | Ibuki |
| 2008/0038561 | A1 | 2/2008 | Yoshizawa et al. |
| 2008/0049431 | A1 | 2/2008 | Boek et al. |
| 2008/0084532 | A1 | 4/2008 | Kurtin |
| 2008/0088793 | A1 | 4/2008 | Sverdrup et al. |
| 2008/0123049 | A1 | 5/2008 | Volk |
| 2008/0144185 | A1 | 6/2008 | Wang et al. |
| 2008/0170299 | A1 | 7/2008 | Kawabata |
| 2008/0171431 | A1 | 7/2008 | Yu et al. |
| 2008/0290435 | A1 | 11/2008 | Oliver et al. |
| 2008/0291394 | A1 | 11/2008 | Ishak |
| 2009/0015786 | A1 | 1/2009 | Harris |
| 2009/0027778 | A1 | 1/2009 | Wu et al. |
| 2009/0096106 | A1 | 4/2009 | Vrtis et al. |
| 2009/0289529 | A1 | 11/2009 | Ito et al. |
| 2009/0304924 | A1 | 12/2009 | Gadgil |
| 2010/0075056 | A1 | 3/2010 | Axisa et al. |
| 2010/0109486 | A1 | 5/2010 | Polyakov et al. |
| 2010/0168409 | A1 | 7/2010 | Fujita |
| 2010/0202054 | A1 | 8/2010 | Niederer |
| 2010/0238400 | A1 | 9/2010 | Volk |
| 2011/0075096 | A1 | 3/2011 | Ishak et al. |
| 2011/0085131 | A1 | 4/2011 | Gupta et al. |
| 2011/0096411 | A1 | 4/2011 | Henriksen et al. |
| 2011/0149410 | A1 | 6/2011 | Blum |
| 2011/0176105 | A1 | 7/2011 | Harris |
| 2011/0179861 | A1 | 7/2011 | Grange et al. |
| 2011/0235326 | A1 | 9/2011 | Yeh et al. |
| 2011/0294305 | A1 | 12/2011 | Jacobs et al. |
| 2012/0029416 | A1 | 2/2012 | Parker et al. |
| 2012/0032559 | A1 | 2/2012 | Hino et al. |
| 2012/0041553 | A1 | 2/2012 | Gupta et al. |
| 2012/0044571 | A1 | 2/2012 | Mukawa |
| 2012/0063000 | A1 | 3/2012 | Batchko et al. |
| 2012/0087015 | A1 | 4/2012 | Nibauer et al. |
| 2012/0092775 | A1 | 4/2012 | Duston et al. |
| 2012/0170920 | A1 | 7/2012 | Moreau et al. |
| 2012/0229754 | A1 | 9/2012 | Iyer et al. |
| 2012/0250151 | A1 | 10/2012 | Lee et al. |
| 2012/0287512 | A1 | 11/2012 | Egan et al. |
| 2013/0171546 | A1 | 7/2013 | White et al. |
| 2013/0176628 | A1 | 7/2013 | Batchko et al. |
| 2013/0300635 | A1 | 11/2013 | White et al. |
| 2014/0009039 | A1 | 1/2014 | Jenninger et al. |
| 2014/0078586 | A1 | 3/2014 | Spurgeon et al. |
| 2014/0153102 | A1 | 6/2014 | Chang |
| 2014/0186215 | A1* | 7/2014 | Shinta .................. G01N 21/658 977/773 |
| 2014/0227548 | A1* | 8/2014 | Myrick .................. C06B 45/30 203/40 |
| 2014/0300857 | A1 | 10/2014 | Cohen-Tannoudji et al. |
| 2014/0312737 | A1 | 10/2014 | Jenninger et al. |
| 2015/0062719 | A1 | 3/2015 | Kyung et al. |
| 2015/0116656 | A1 | 4/2015 | Stevens et al. |
| 2015/0138110 | A1 | 5/2015 | Yairi et al. |
| 2015/0146161 | A1 | 5/2015 | Rigato et al. |
| 2015/0302990 | A1 | 10/2015 | Ghosh et al. |
| 2015/0323812 | A1 | 11/2015 | Ishak et al. |
| 2016/0004099 | A1 | 1/2016 | Steven et al. |
| 2016/0091635 | A1 | 3/2016 | Ibuki et al. |
| 2016/0187985 | A1 | 6/2016 | Lim et al. |
| 2017/0021385 | A1* | 1/2017 | Smith .................... B05D 1/12 |
| 2017/0045649 | A1 | 2/2017 | Bolis |
| 2017/0160600 | A1 | 6/2017 | Galstian et al. |
| 2017/0177106 | A1 | 6/2017 | Kihara |
| 2017/0184848 | A1 | 6/2017 | Vallius |
| 2017/0188021 | A1 | 6/2017 | Lo et al. |
| 2017/0192595 | A1 | 7/2017 | Choi et al. |

(56) References Cited

U.S. PATENT DOCUMENTS

| | | | |
|---|---|---|---|
| 2017/0261653 | A1 | 9/2017 | Peyman |
| 2017/0299956 | A1 | 10/2017 | Holland et al. |
| 2017/0317269 | A1 | 11/2017 | Zhang et al. |
| 2017/0336641 | A1 | 11/2017 | Von Und Zu Liechtenstein |
| 2018/0255250 | A1 | 9/2018 | Price et al. |
| 2018/0275394 | A1 | 9/2018 | Yeoh et al. |
| 2018/0335649 | A1 | 11/2018 | Tsai |
| 2019/0173128 | A1* | 6/2019 | Visco ............... H01M 50/403 |
| 2019/0243123 | A1 | 8/2019 | Bohn |
| 2019/0302479 | A1 | 10/2019 | Smyth et al. |
| 2020/0166742 | A1 | 5/2020 | Peyman |
| 2020/0251709 | A1* | 8/2020 | Lee .................... B01D 67/00 |

FOREIGN PATENT DOCUMENTS

| | | |
|---|---|---|
| WO | 2008/156166 A1 | 12/2008 |
| WO | 2010/078666 A1 | 7/2010 |
| WO | 2010/104904 A2 | 9/2010 |
| WO | 2019/183431 A1 | 9/2019 |
| WO | 2019/190887 A1 | 10/2019 |

OTHER PUBLICATIONS

Ding et al., "Surface profiling of an aspherical liquid lens with a varied thickness membrane," Optics Express 3122-3132, vol. 25, No. 4 (Feb. 6, 2017).
Jiang et al., Transparent Electro-Optic Ceramics and Devices, Optoelectronic devices and integration, pts 1 and 2 SPIE-Int Soc Optical Engineering, Bellingham, pp. 380-394 (Jan. 17, 2005).
Keplinger et al., Stretchable, Transparent, Ionic Conductors, Science Magazine, vol. 341, pp. 984-987 (Aug. 30, 2013).
Kong et al., Transparent Ceramics, Topics in Mining, Metallurgy, and Materials Engineering, Ch. 2: Transparent Ceramic Materials, pp. 29-91 (2015).
Patra et al., Comparison on Optical Properties of Pure and Doped Lithium Tetraborate Single Crystals and Glasses, Solid State Physics: Proceedings of the 56th DAE Solid State Physics Symposium 2011, AIP Conf. Proc. 1447, 1335-46 (Dec. 11, 2012).
Zhao et al., "Spherical aberration free liquid-filled tunable lens with variable thickness membrane," Optics Express 21264-21278, vol. 23, No. 16. (Aug. 5, 2015).
Non-Final Office Action received for U.S. Appl. No. 16/016,428 dated Mar. 12, 2021, 56 pages.
Non-Final Office Action received for U.S. Appl. No. 16/035,562 dated Jun. 10, 2021, 36 pages.
Non-Final Office Action received for U.S. Appl. No. 16/016,428 dated Jun. 16, 2021, 43 pages.
Notice of Allowance received for U.S. Appl. No. 15/972,794 dated Oct. 16, 2020, 22 pages.
Notice of Allowance received for U.S. Appl. No. 15/992,731 dated Nov. 18, 2020, 37 pages.
Final Office Action received for U.S. Appl. No. 16/106,945 dated Nov. 24, 2020, 94 pages.
Final Office Action received for U.S. Appl. No. 16/018,752 dated Nov. 30, 2020, 41 pages.
Notice of Allowance received for U.S. Appl. No. 16/018,746 dated Nov. 3, 2020, 39 pages.
Notice of Allowance received for U.S. Appl. No. 16/021,580 dated Dec. 9, 2020, 68 pages.
Preinterview First Office Action received for U.S. Appl. No. 16/021,650 dated Feb. 1, 2021, 47 pages.
Gurvich, Mark R., "On Characterization of Anisotropic Elastomeric Materials for Structural Analysis", Rubber Chemistry and Technology, vol. 77, No. 1, 2004, pp. 115-130.
Non-Final Office Action received for U.S. Appl. No. 16/106,945 dated Mar. 30, 2021, 111 pages.
Notice of Allowance received for U.S. Appl. No. 16/018,752 dated Mar. 10, 2021, 32 pages.
Non-Final Office Action received for U.S. Appl. No. 16/013,837 dated Jan. 23, 2020, 22 pages.
Notice of Allowance received for U.S. Appl. No. 16/013,837 dated Apr. 14, 2020, 14 pages.
Preinterview First Office Action received for U.S. Appl. No. 15/992,731 dated Sep. 27, 2019, 17 pages.
Final Office Action received for U.S. Appl. No. 15/992,731 dated Jun. 2, 2020, 25 pages.
Non-Final Office Action received for U.S. Appl. No. 15/992,731 dated Aug. 24, 2020, 27 pages.
Examiner-Initiated Interview Summary received for U.S. Appl. No. 16/008,635 dated Apr. 20, 2020, 3 pages.
Notice of Allowance received for U.S. Appl. No. 16/008,635 dated May 4, 2020, 32 pages.
Non-Final Office Action received for U.S. Appl. No. 16/059,091 dated Apr. 8, 2020, 54 pages.
Final Office Action received for U.S. Appl. No. 16/059,091 dated Sep. 21, 2020, 18 pages.
Non-Final Office Action received for U.S. Appl. No. 16/106,945 dated Apr. 16, 2020, 59 pages.
Non-Final Office Action received for U.S. Appl. No. 16/041,634 dated Jul. 30, 2020, 24 pages.
Notice of Allowance received for U.S. Appl. No. 16/041,634 dated Aug. 28, 2020, 31 pages.
Preinterview First Office Action received for U.S. Appl. No. 16/018,752 dated Dec. 16, 2019, 19 pages.
Preinterview First Office Action received for U.S. Appl. No. 16/018,746 dated Jul. 14, 2020, 20 pages.
Notice of Allowance Action received for U.S. Appl. No. 16/018,746 dated Sep. 17, 2020, 24 pages.
Preinterview First Office Action received for U.S. Appl. No. 16/021,580 dated Aug. 4, 2020, 48 pages.
"Adjustable Reading Glasses," URL: https://adlens.com/, retrieved on May 7, 2018, 1 page.
Guha et al., "Creating nanoscale emulsions using condensation", Nature Communications, vol. 8, No. 1371, Nov. 2017, pp. 1-7.
Merriam-Webster, "Porosity", URL: https://www.merriam-webster.com/dictionary/porosity, retrieved on Apr. 8, 2020, pp. 1-8.
International Search Report and Written Opinion received for PCT Application Serial No. PCT/US2019/023484 dated Jul. 3, 2019, 9 pages.
International Preliminary Report on Patentability received for PCT Application Serial No. PCT/US2019/023484 dated Oct. 1, 2020, 8 pages.
International Search Report and Written Opinion received for PCT Application Serial No. PCT/US2019/023485 dated Jul. 4, 2019, 11 pages.
International Preliminary Report on Patentability received for PCT Application Serial No. PCT/US2019/023485 dated Oct. 8, 2020, 8 pages.
"Adaptive Glasses," Press Kit Home, Retrieved on Mar. 13, 2018, 5 pages, Retrieved from the Internet: URL: http://tvc.utah.edu/ces/press-kit.php.
"Adjustable Lens Glasses: How They Work," UZOOM Adlens, Retrieved on Mar. 28, 2018, 9 pages, Retrieved from the Internet: URL: https://adlens.com/how-it-works/.
Billah M., et al., "Microstructure Evolution and Electrical Characterization of Lanthanum Doped Barium Titanate (BaTiO3) Ceramics," International Conference on Mechanical Engineering, AIP Conference Proceedings 1754, Jul. 12, 2016, Article 030006, pp. 1-7.
Communication pursuant to Article 94(3) EPC for European Patent Application No. 19715707.6, dated Mar. 22, 2021, 5 pages.
Cooke J.M., et al., "Optical Lens Assemblies, Head-Mounted Displays, and Methods of Altering Optical Properties of Optical Lens Assemblies," U.S. Appl. No. 16/013,837, filed Jun. 20, 2018, 67 pages.
Cooke J.M., et al., "Optical Lens Assemblies, Head-Mounted Displays, and Related Methods," U.S. Appl. No. 16/021,580, filed Jun. 28, 2018, 49 pages.
"Displacement Modes of Piezoelectric Actuators," Piezo Technology, Retrieved on Mar. 14, 2018, 12 pages, Retrieved from the

(56) References Cited

OTHER PUBLICATIONS

Internet: URL: https://www.piceramic.com/enpiezo-technology/properties-piezo-actuators/displacement-modes/.

"Focus Tunable Lenses," Optotune, Mar. 13, 2018, 2 Pages, Retrieved from the Internet: URL: http://www.optotune.com/technology/focus-tunable-lenses.

He C., et al., "Linear Electro-Optic Properties of Orthorhombic PZN-8%PT Single Crystal," IEEE Transactions on Ultrasonics, Ferroelectrics, and Frequency Control, Jun. 1, 2011, vol. 58 (6), pp. 1118-1121.

"Highly Reliable Multilayer Piezo Actuators," Piezo Technology, Retrieved on Mar. 14, 2018, 8 pages. Retrieved from the Internet: URL: https://www.piceramic.com/en/piezo-technology/picma/.

Hocking L.M., "The Effect of Slip on the Motion of a Sphere Close to a Wall and of Two Adjacent Spheres," Journal of Engineering Mathamatics, 1973, vol. 7 (3), pp. 207-221.

"How Does it Work," Polight, Retrieved on Mar. 13, 2018, 3 pages, Retrieved from the Internet: URL: http://www.polight.com/technology-and-products/how-does-it-work/default.aspx.

Knapp K., et al., "Understanding Zirconia Crown Esthetics and Optical Properties," Retrieved on Jun. 12, 2018, vol. 2 (4), 17 pages, Retrieved from the Internet: URL: http://glidewelldental.com/education/inclusive-dental-implant-magazine-volume-2-issue-4/.

Ouderkirk A.J., et al., "Apparatuses, Systems, and Methods for Adjusting Fluid Lenses," U.S. Appl. No. 16/008,635, filed Jun. 14, 2018, 41 Pages.

Ouderkirk A.J., et al., "Electroactive Polymer Devices and Nanovoided Polymer Materials and Methods and Systems fabrication Thereof," U.S. Appl. No. 16/106,945, filed Aug. 21, 2018, 98 pages.

Ouderkirk A.J., et al., "Electroactive Polymer Devices, Systems, and Methods," U.S. Appl. No. 16/035,562, filed Jul. 13, 2018, 55 Pages.

Ouderkirk A.J., et al., "Electroactive Polymer Devices, Systems, and Methods," U.S. Appl. No. 16/059,091, filed Aug. 9, 2018, 68 Pages.

Ouderkirk A.J., et al., "Multi-Element Prescription Lenses With Eye-Tracking," for U.S. Appl. No. 16/041,634, filed Jul. 20, 2018, 87 Pages.

Ouderkirk A.J., et al., "Optical Lens Assemblies and Related Methods," U.S. Appl. No. 16/018,752, filed Jun. 26, 2018, 35 pages.

Ouderkirk A.L., et al., "Optical Devices, Systems, and Methods of Manufacturing," U.S. Appl. No. 62/646,900, filed Mar. 22, 2018, 13 pages.

Ouderkirk A.L., et al., "Optical Devices, Systems, and Methods of Manufacturing," U.S. Appl. No. 62/650,254, filed Mar. 29, 2018, 9 pages.

"Piezoelectric Materials, New Materials, Piezo Theory," APC International, Ltd., Retrieved on Mar. 15, 2018, 1 page, Retrieved from the Internet: URL: https://www.americanpiezo.com/knowledge-center/piezo-theory/new-materials.html.

Riegler B., et al., "Index Matching Silicone for High Brightness LED Packaging," IMAPS International Conference on Device Packaging, Mar. 13-16, Scottsdale, AZ., Mar. 18, 2005, 17 Pages.

Shian S., et al., "Tunable Lenses using Transparent Dielectric Elastomer Actuators," School of Engineering and Applied Sciences, Harvard University, Cambridge, Masschusetts 02138, USA, Optics Express, Mar. 26, 2013, vol. 21 (7), 8 pages.

Smyth K.M., et al., "Optical Lens Assemblies and Related Methods," U.S. Appl. No. 16/018,746, filed Jun. 26, 2018, 45 pages.

Smyth K.M., et al., "Optical Lens Assemblies, Head-Mounted Displays, and Related Methods," U.S. Appl. No. 16/016,428, filed Jun. 22, 2018, 78 pages.

Smyth K.M., et al., "Optical Lens Assemblies, Head-Mounted Displays, and Related Methods," U.S. Appl. No. 16/021,650, filed Jun. 28, 2018, 52 pages.

Smyth K.M., et al., "Systems and Methods for Actuation of Asymmetric Optical Elements," U.S. Appl. No. 15/992,731, filed May 30, 2018, 65 pages.

Wang Y., et al., "A Highly Stretchable, Transparent, and Conductive Polymer," Science Advances, Mar. 10, 2017, vol. 3 (3), Article e1602076, pp. 1-10.

\* cited by examiner

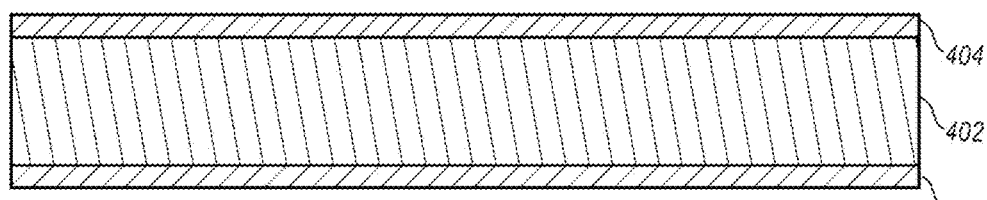
FIG. 4A
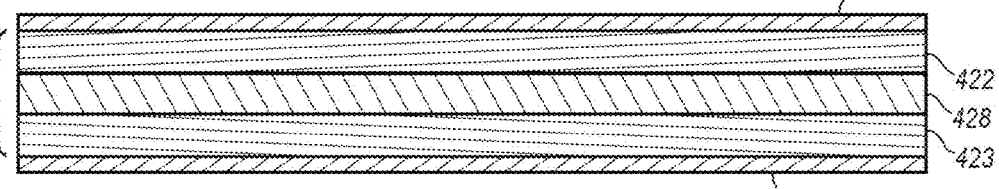
FIG. 4B
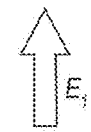
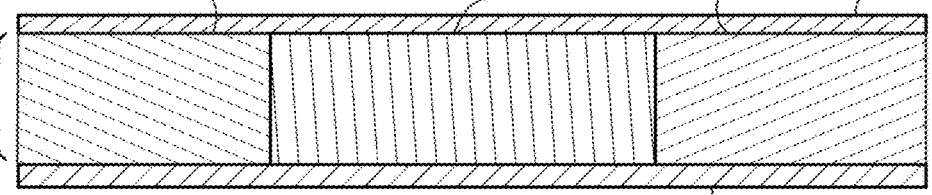
FIG. 4C
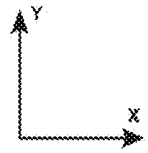

NANOVOIDED ELECTROACTIVE POLYMER DEVICES, SYSTEMS, AND METHODS

CROSS REFERENCE TO RELATED APPLICATIONS

This application is a non-provisional utility application which claims the benefit of U.S. Provisional Application No. 62/646,900 filed 22 Mar. 2018 and U.S. Provisional Application No. 62/650,254 filed 29 Mar. 2018, the disclosures of each of which are incorporated, in their entirety, by this reference.

BACKGROUND

Electroactive polymer (EAP) materials include materials that may change their shape in the presence of an electric field, thus exhibiting electromechanical coupling. There are several conventional subspecies of these materials such as electrostrictive polymers, piezoelectric polymers, and dielectric polymers. A common EAP is a dielectric elastomer. A separate category of EAPs may include those that change their shapes due to intermolecular ion transactions. While EAP materials may be functionally similar to piezoelectric materials in some respects, EAP materials may exhibit considerably different electromechanical response characteristics.

EAP materials have been investigated for use in various technologies, including actuation and/or energy harvesting applications. Unfortunately, the energy density and, in some applications, the specific power density of electroactive polymers in practical devices are commonly considerably lower than for other materials, such as lead-containing PZT and its variations. Thus, there is a need for increasing both the energy density and specific power density of electroactive devices.

SUMMARY

As will be described in greater detail below, the instant disclosure describes electroactive devices that include nanovoided polymer materials, and associated systems and methods. For example, an electroactive device may include (1) an electroactive polymer element having a first surface and a second surface opposite the first surface, the electroactive polymer element including a nanovoided polymer material, (2) a primary electrode abutting the first surface of the electroactive polymer element, and (3) a secondary electrode abutting the second surface of the electroactive polymer element. The electroactive polymer element may be deformable from an initial state to a deformed state by application of an electrostatic field produced by a potential difference between the primary electrode and the secondary electrode. Various other devices, systems, and methods are also disclosed.

According to some embodiments, the deformed state of the electroactive polymer element may be a compressed state. The nanovoided polymer material may define a plurality of voids having diameters of from approximately 10 nm to approximately 1 μm. In some examples, the nanovoided polymer material may define a plurality of voids collectively occupying from approximately 10% by volume to approximately 90% by volume of the nanovoided polymer material when the electroactive polymer element is in an undeformed state. According to at least one example, the electroactive polymer element may have a maximum thickness of from approximately 100 nm to approximately 10 μm in an undeformed state and each of the primary electrode and the secondary electrode may have a thickness of from approximately 10 nm to approximately 1 μm. The nanovoided polymer material may include a polymer having an elastic modulus of approximately 10 GPa or less.

In some embodiments, an electroactive device may include (1) a primary electrode, (2) a secondary electrode overlapping the primary electrode, (3) a tertiary electrode overlapping the primary electrode and the secondary electrode, (4) a first electroactive polymer element disposed between and abutting the primary electrode and the secondary electrode, the first electroactive polymer element including a nanovoided polymer material, and (5) a second electroactive polymer element disposed between and abutting the secondary electrode and the tertiary electrode, the second electroactive polymer element including a nanovoided polymer material. The first electroactive polymer element may be deformable from an initial state to a deformed state when a first electrostatic field is generated between the primary electrode and the secondary electrode and the second electroactive polymer element may be deformable, in conjunction with deformation of the first electroactive polymer element, from an initial state to a deformed state when a second electrostatic field is generated between the secondary electrode and the tertiary electrode. In some examples, the first electrostatic field may be substantially equal to the second electrostatic field.

A corresponding method may include (1) positioning an electroactive polymer element on a primary electrode such that the primary electrode abuts a first surface of the electroactive polymer element, the electroactive polymer element including a nanovoided polymer material, and (2) positioning a secondary electrode on the electroactive polymer element such that a second surface of the electroactive polymer element opposite the first surface abuts the secondary electrode. The electroactive polymer element may be deformable from an initial state to a deformed state when a voltage is applied between the primary electrode and the secondary electrode.

According to at least one embodiment, the method also include forming the electroactive polymer element including the nanovoided polymer material by (1) depositing a mixture including a curable material and a solvent, (2) curing the curable material to form a cured polymer material including the solvent in a plurality of defined solvent regions, and (3) removing at least a portion of the solvent from the cured polymer material. In this example, removing at least the portion of the solvent from the cured polymer material may form a plurality of voids in the resulting nanovoided polymer material. In some examples, the curable material may include an acrylate material and the mixture may further include a free radical initiator of at least one of a thermal initiator or an ultraviolet initiator. Additionally or alternatively, the cured polymer material may include a silicone-based polymer material. In this example, the mixture may further include a hydrosilylation catalyst. In various examples, the cured polymer material may include poly (dimethylsiloxane). In various embodiments, depositing the mixture including the curable material and the solvent may further include depositing the mixture on the primary electrode. Additionally or alternatively, depositing the mixture including the curable material and the solvent may further include depositing the mixture by at least one of spin coating or inkjet deposition.

In various embodiments, the method may further include forming the electroactive polymer element including the nanovoided polymer material by (1) depositing a mixture that includes a curable material and a cavitation agent, (2) exposing the mixture to a form of radiation sufficient to cure the curable material and decompose the cavitation agent to form a cured polymer material including one or more decomposition products of the cavitation agent in a plurality of defined regions, and (3) removing at least a portion of the one or more decomposition products from the cured polymer material. In this example, the cavitation agent may include a beta-keto acetic acid. In various examples, the mixture may also include a solvent and the cured polymer material may further include the solvent in the plurality of defined regions.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

FIGS. 4A-4C are cross-sectional views of exemplary electroactive devices in accordance with some embodiments.

DETAILED DESCRIPTION OF EXEMPLARY EMBODIMENTS

Figure 1:
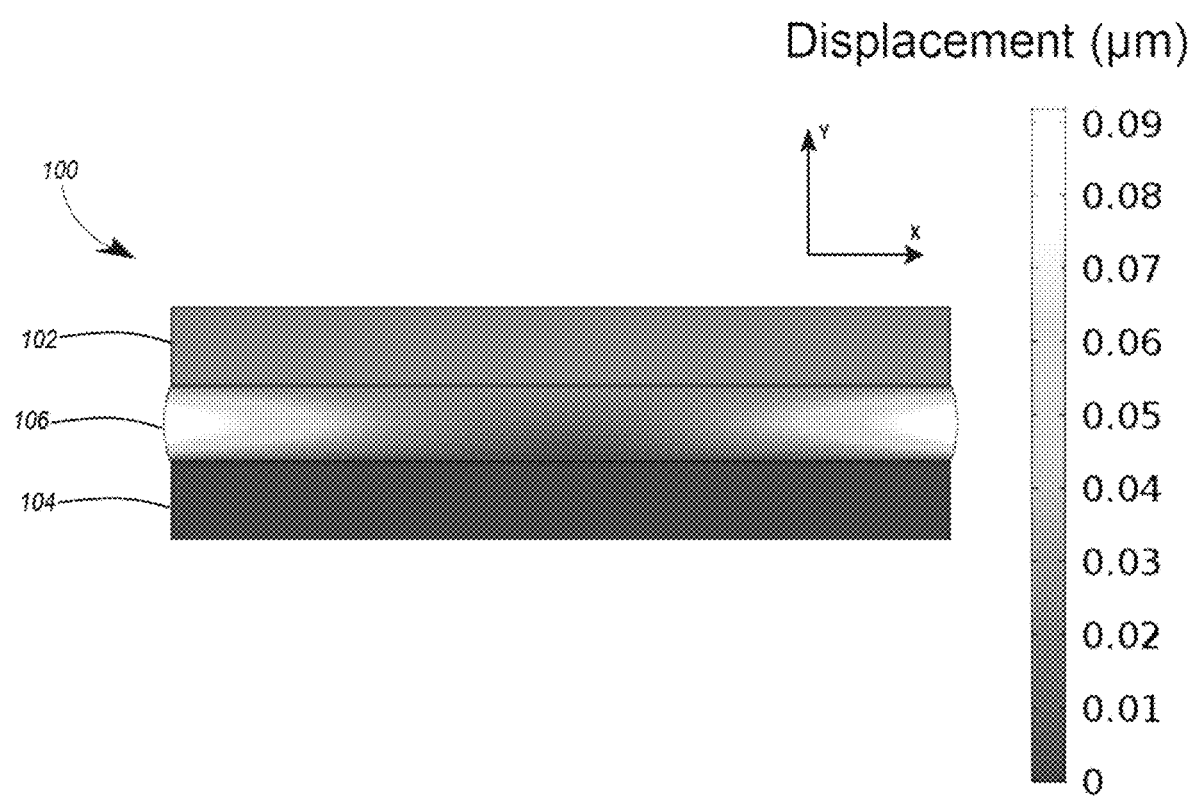
FIG. 1 is a cross-sectional view of an electroactive device.

The present disclosure describes various electroactive devices, systems, and corresponding methods. As will be explained in greater detail below, embodiments of the instant disclosure may include an electroactive device having an electroactive polymer element with a first surface and a second surface opposite the first surface. The electroactive device may also include paired electrodes, such as a primary electrode abutting the first surface of the electroactive polymer element and a secondary electrode abutting the second surface of the electroactive polymer element. The electroactive polymer element may include a nanovoided polymer material that is deformable from an undeformed state or partially deformed state to a more fully deformed state, such as a compressed state, when a voltage difference is applied between the primary electrode and the secondary electrode such that the electroactive polymer element experiences substantially greater strains, concomitantly with less associated stress, thus increasing the energy density and of disclosed electroactive devices. Such electroactive devices may experience greater degrees of deformation in comparison to conventional devices, allowing for increased translational movement of surface portions of the electroactive devices.

The following will provide, with reference to FIGS. 1, 3, 4, and 13-15, examples of electroactive devices. In addition, the discussion corresponding to FIGS. 2 and 5-12 will provide examples of characteristics exhibited by various electroactive devices. Finally, the discussion corresponding to FIGS. 16-18 will provide examples of methods for forming electroactive devices and nanovoided polymer materials.

According to some embodiments, an electroactive polymer (EAP) may be a deformable polymer material that deforms (e.g., compress, elongates, bends, etc.) via a force created by an electrostatic field. The EAP may be symmetric with regard to electrical charge (e.g., polydimethylsiloxane (PDMS), acrylates, etc.) or asymmetric (e.g., poled polyvinylidene fluoride (PVDF) or its copolymers, such as poly (vinylidenefluoride-co-trifluoroethylene) (PVDF-TrFE), etc.). In the presence of an electrostatic field, an EAP may deform according to the strength of that field. Generation of such a field may be accomplished by placing the EAP between two electrodes, each of which is at a different potential. As the potential difference (i.e., voltage difference) between the electrodes is increased (e.g., from zero potential) the amount of deformation may also increase, principally along electric field lines. This deformation may achieve saturation when a certain electrostatic field strength has been reached. With no electrostatic field, the EAP may be in its relaxed state undergoing no induced deformation, or stated equivalently, no induced strain, either internal or external.

The physical origin of the compressive nature of EAP in the presence of an electrostatic field (E-field), being the force created between opposite electric charges, is that of the Maxwell stress, which is expressed mathematically with the Maxwell stress tensor. The level of strain or deformation induced by a given E-field is dependent on the square of the E-field strength, the dielectric constant of the EAP, and on the elastic compliance of the material in question. Compliance in this case is the change of strain with respect to stress or, equivalently, in more practical terms, the change in displacement with respect to force.

Electroactive devices described herein may be devices that convert electrical energy to mechanical energy and/or devices that convert mechanical energy to electrical. Examples of electroactive devices may include, without limitation, actuators, sensors, microelectromechanical devices, and/or any other suitable devices. In various embodiments, electroactive devices may include paired electrodes, which allow the creation of the electrostatic field that forces constriction of the EAP. Such electrodes may include relatively thin, electrically conductive layers or elements and may be of a non-compliant or compliant nature. Any suitable materials may be utilized in the electrodes, including electrically conductive materials suitable for use in thin-film electrodes, such as, for example, aluminum, transparent conductive oxides, silver, indium, gallium, zinc, carbon nanotubes, carbon black, and/or any other suitable materials formed by vacuum deposition, spray, adhesion, and/or any other suitable technique either on a non-EAP layer or directly on the EAP surface itself. In some embodiments, the electrode or electrode layer may be self-healing, such that damage from local shorting of a circuit can be isolated. Suitable self-healing electrodes may include thin films of metals, such as, for example, aluminum.

According to at least one embodiment, an electroactive device may include an EAP element having a first surface and a second surface opposite the first surface. The electroactive device may also include paired electrodes, including a primary electrode abutting (i.e., touching, in physical contact with, adhered to, and/or in close proximity to) the first surface of the EAP element and a secondary electrode abutting the second surface of the EAP element.

EAP elements, without external dimensional constraints, may contract along electrostatic E-field lines and expand in transverse dimensions. This expansion may cause strain non-uniformities, and thus lowering the energy density and specific power density away from the theoretically achievable limits. Embodiments presented herein may overcome these limitations, providing an electroactive device of greater energy density and/or deformability (e.g., compressibility).

An example of the afore-described deficiencies is illustrated in FIG. 1, which demonstrates a significant gap between theoretical predictions and practical performance. This figure shows an electroactive device 100 that includes a movable electrode 102 and a fixed electrode 104 that are spaced with an EAP element 106 including PDMS positioned therebetween. In this exemplary embodiment, EAP element 106 in an undeformed state is 1 μm thick along a direction (i.e., along the Y-direction shown in FIG. 1) between movable electrode 102 and fixed electrode 104. In the exemplary embodiment shown in FIG. 1, a width (i.e., a width in the X-direction shown in FIG. 1) of each of movable electrode 102, fixed electrode 104, and EAP element 106 in the undeformed state is 10 μm. As shown in FIG. 1, the relatively small displacement (approximately 0.03 microns) in the X-direction of movable electrode 102, requires a substantially larger displacement (approximately 0.09 microns) of EAP element 106 due to compression of EAP element 106 near the lateral edges of EAP element 106 in comparison to inner portions of EAP element 106 disposed away from the lateral edges when an electrostatic field is generated between movable electrode 102 and fixed electrode 104. The amount of displacement of EAP element 106 required to achieve a particular displacement of movable electrode 102 increases as the width of electroactive device 100 increases.

Figure 2:
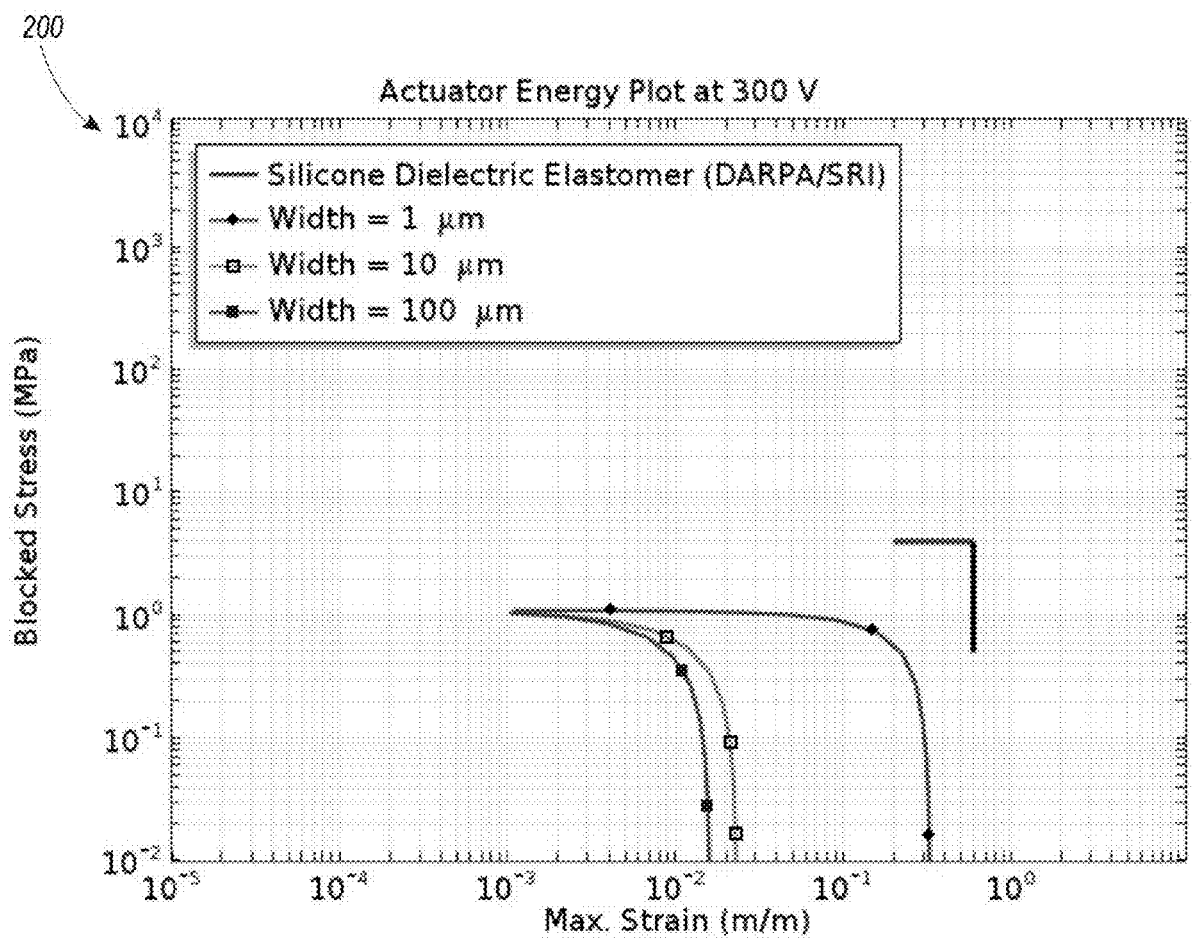
FIG. 2 is a graph showing the impact of changing aspect ratio of an exemplary actuator (width to thickness) including an electroactive element with other factors being held constant in accordance with some embodiments.

FIG. 2 shows the blocked stress as a function of strain for electroactive devices having EAP elements disposed between paired electrodes (see, e.g., FIG. 1). The electroactive devices represented in FIG. 2 are electroactive actuators having 1, 10, and 100 μm widths, all with an EAP element thickness of 1 μm and an applied voltage of 300V. The EAP material in this case is PDMS. The EAP elements were modeled with a neo-Hookean model with the Lame parameter, being 100 MPa and the Lame parameter μ being 1 MPa. As can be seen by inspection of the FIG. 2 curves for the 10 and 100 μm widths, the practical maximum energy is about 100 times less than the theoretical prediction for a silicone dielectric elastomer. This theoretical prediction is depicted as two solid lines in the upper right-hand corner and referenced in the FIGS. 2 and 5-7 as DARPA.

Increases in energy density and overall deformation and displacement of EAP elements, resulting, for example, in increased displacement of abutting movable electrodes, may be accomplished by using voided polymers, such as nanovoided polymers, as the electroactive material in electroactive devices. Nanovoided polymers may provide a mechanism to improve the efficiency and effectiveness of actual EAP device performance. As will be described in greater detail below, such an electroactive device may include a primary and a secondary electrode layer or surface and a polymer layer (e.g., an EAP element) that may include a nanovoided polymer material interposed between at least a portion of the volume between the first and the second electrodes. Alternatively, the polymer layer between the electrodes may be entirely of voided and/or nanovoided material. Additionally, disposed between an electrode and its adjacent nanovoided polymer material may be a dielectric material with a suitable dielectric constant or relative permittivity, such as, for example, a dielectric constant between approximately 2 and approximately 30.

The voids may be any suitable size and, in some embodiments, the voids may approach the scale of the thickness of the polymer layer in the undeformed state. For example, the voids may be between approximately 10 nm to about equal to the gap between the paired two electrodes. In some embodiments, the voids may be between approximately 10 nm and approximately 1000 nm, such as between approximately 10 and approximately 200 nm (e.g., approximately 10 nm, approximately 20 nm, approximately 30 nm, approximately 40 nm, approximately 50 nm, approximately 60 nm, approximately 70 nm, approximately 80 nm, approximately 90 nm, approximately 100 nm, approximately 110 nm, approximately 120 nm, approximately 130 nm, approximately 140 nm, approximately 150 nm, approximately 160 nm, approximately 170 nm, approximately 180 nm, approximately 190 nm, approximately 200 nm, approximately 250 nm, approximately 300 nm, approximately 400 nm, approximately 500 nm, approximately 600 nm, approximately 700 nm, approximately 800 nm, approximately 900 nm, approximately 1000 nm).

The voids may be either closed- or open-celled, or a mixture thereof. If they are open-celled, the void size may be the minimum average diameter of the cell. In some embodiments, the polymer layer may include a thermoset material and/or any other suitable material having an elastic modulus of less than approximately 10 GPa (e.g., approximately 0.5 GPa, approximately 1 GPa, approximately 2 GPa, approximately 3 GPa, approximately 4 GPa, approximately 5 GPa, approximately 6 GPa, approximately 7 GPa, approximately 8 GPa, approximately 9 GPa). In some embodiments, the nanovoided polymer material may define a plurality of voids collectively occupying from approximately 10% by volume to approximately 90% by volume, such as from approximately 30% by volume to approximately 70% by volume (e.g., approximately 10% by volume, approximately 20% by volume, approximately 30% by volume, approximately 40% by volume, approximately 50% by volume, approximately 60% by volume, approximately 70% by volume, approximately 80% by volume, approximately 90% by volume) of the nanovoided polymer material when the electroactive polymer, e.g., PDMS, is in an undeformed state.

Figure 3A:
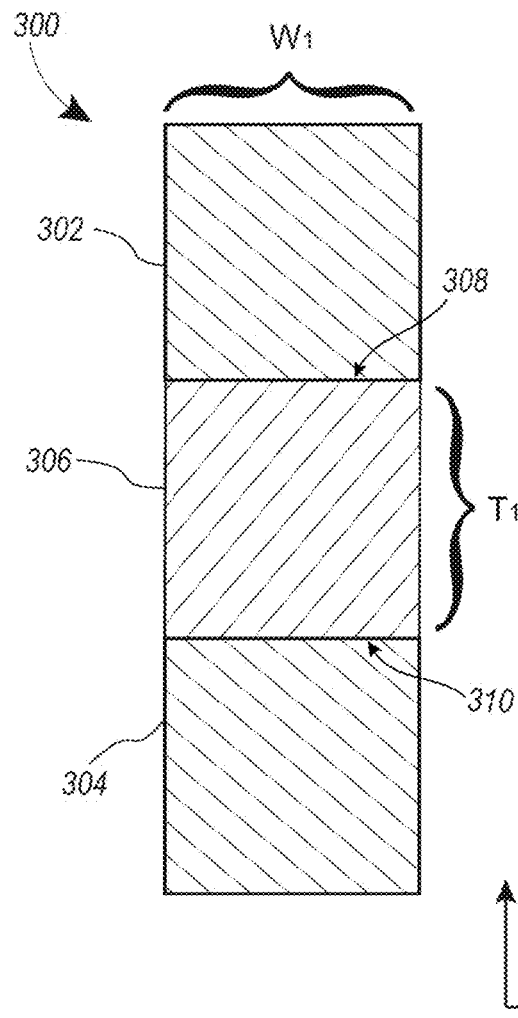
FIGS. 3A and 3B are cross-sectional views of an exemplary electroactive device according to at least one embodiment.
Figure 3B:
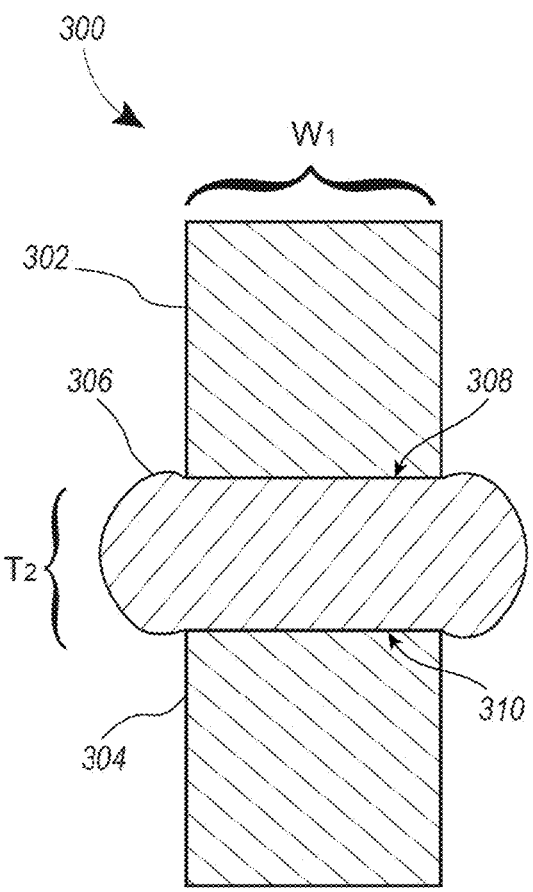

In an exemplary embodiment, as shown in FIGS. 3A and 3B, electroactive device 300 may include a pair of electrodes including a primary electrode 302 and a secondary electrode 304. These paired electrodes are spaced with an EAP element 306 formed of an electroactive nanovoided polymer positioned therebetween such that primary electrode 302 abuts a first surface 308 of nanovoided EAP element 306 and secondary electrode 304 abuts a second surface 310 of nanovoided EAP element 306 opposite the first surface. In some embodiments, a ratio of a width Wi of the EAP element to a thickness $T_1$ (i.e., in the Y-direction shown in FIG. 3A) of the EAP element between the paired electrodes may be lower than that illustrated in FIG. 1 such that the EAP element is deformed in a more uniform manner than EAP element 106 of electroactive device 100 illustrated in FIG. 1. EAP element 306 may additionally or alternatively have any suitable dimensions, including any suitable thickness and/or width, without limitation.

In some embodiments, EAP element 306 may be deformable from an undeformed state, as illustrated in FIG. 3A, or a partially deformed state to a more fully deformed state, as illustrated in FIG. 3B, when a voltage difference is applied between primary electrode 302 and secondary electrode 304 such that the energy density of EAP element 306 is greater than if EAP element 306 consisted of non-nanovoided polymer material. In some embodiments, the deformed state of EAP element 306 may be a compressed state in which EAP element 306 has a decreased thickness $T_2$ in the Y-direction, as shown in FIG. 3B. Thickness, as used herein, may refer to the extent of at least a portion of an EAP element parallel to an E-field generated between paired electrodes abutting the EAP element. In some embodiments, the initial state of EAP element 306 may be a state that is not influenced by an E-field or one already influenced by an E-field generated between primary electrode 302 and secondary electrode 304, and the E-field may be increased to amplify the E-field-induced deformations. An exemplary direction $E_1$ of the lines of the electrostatic field between electrode 302 and electrode 304 is represented in FIGS. 3A and 3B. According to some embodiments, an amount of deformation of EAP element 306 in the deformed state, as shown in FIGS. 3A and 3B, may correspond to the strength of the E-field or, equivalently, an amount of voltage applied between primary electrode 302 and secondary electrode 304.

In at least one example, when EAP element 306 is in a compressed state, EAP element may expand laterally (i.e., in the X-direction shown in FIG. 3A) such that EAP element has an increased width in the X-direction. In some embodiments, EAP element 306 may be initially stretched in the X-direction.

EAP element 306 may have a maximum thickness (e.g., thickness $T_1$ shown in FIG. 3A) in an undeformed or relaxed state and a minimum thickness (e.g., thickness $T_2$ shown in FIG. 3B) in a deformed state (e.g., a maximally deformed state) when a voltage difference of at least a certain value is applied between primary electrode 302 and secondary electrode 304. In some embodiments the maximum thickness of EAP element 306 may be from approximately 10 nm to approximately 10 µm (e.g., approximately 10 nm, approximately 20 nm, approximately 30 nm, approximately 40 nm, approximately 50 nm, approximately 60 nm, approximately 70 nm, approximately 80 nm, approximately 90 nm, approximately 100 nm, approximately 200 nm, approximately 300 nm, approximately 400 nm, approximately 500 nm, approximately 600 nm, approximately 700 nm, approximately 800 nm, approximately 900 nm, approximately 1 µm, approximately 2 µm, approximately 3 µm, approximately 4 µm, approximately 5 µm, approximately 6 µm, approximately 7 µm, approximately 8 µm, approximately 9 µm, approximately 10 µm). Additionally, or alternatively, a width of EAP element 306 in the undeformed state may be from approximately 100 nm to approximately 100 µm (e.g., approximately 100 nm, approximately 500 nm, approximately 1 µm, approximately 10 µm, approximately 20 µm, approximately 30 µm, approximately 40 µm, approximately 50 µm, approximately 60 µm, approximately 70 µm, approximately 80 µm, approximately 90 µm, approximately 100 µm). Width, as used herein, may refer to the extent of at least a portion of an EAP element in a dimension transverse to that of the expected electrostatic field.

EAP element 306 may include any suitable polymeric material, including, for example, an elastomeric polymer such as polydiymethylsiloxane (PDMS). Exemplary embodiments presented hereinbelow specify PDMS as a generic electroactive polymer, but family members and subspecies are applicable as well. PDMS may possesses various characteristics, such as, for example, high transparency, low stiffness, and/or high elasticity. Additional examples of polymer materials forming EAP element 306 may include, without limitation, acrylates, styrenes, polyesters, polycarbonates, epoxies, halogenated polymers, such as PVDF, copolymers of PVDF, such as PVDF-TrFE, silicone polymers, and/or any other suitable polymer materials. Dielectric constants of such materials utilized in EAP elements may range, for example, from approximately 2 to approximately 30.

In at least one embodiment, a dielectric material (i.e., an insulating material) may be disposed between EAP element 306 and at least one of primary electrode 302 or secondary electrode 304. For example, a dielectric coating or layer may be applied to primary electrode 302 and/or secondary electrode 304 such that the dielectric coating is disposed between the corresponding electrode and its associated surface of EAP element 306. Dielectric constants of such dielectric coatings may range, for example, from approximately 2 to approximately 30. In some embodiments, EAP elements may have a 2-dimensional extruded shape or a 3-dimensional shape (e.g., a 3D patterned shape).

FIGS. 4A-C represent depictions of three exemplary embodiments, including, respectively, primary electrodes 404, 424, and 444 and secondary electrodes 406, 426, and 446. Disposed vertically between each of these primary/secondary electrode pairs are one or more layers of EAP material. In FIG. 4A, a single layer of EAP material forming EAP element 402 may include a voided or nanovoided polymer of a certain contribution by volume (e.g., 10-90%).

In FIG. 4B, EAP element 421 disposed between the primary and secondary electrodes 424 and 426 may include multiple polymer layers, such as three separate polymer layers shown in this figure: a center polymer layer 428 of a first composition disposed between outer polymer layers 422 and 423, which may be of the same composition, a second composition, or second and third compositions, respectively. At least one of polymer layers 422, 428, or 423 of EAP element 421 may include a voided or nanovoided electroactive polymer material.

In FIG. 4C, EAP element 441 may include three or more separate EAP polymer layers disposed between primary and secondary electrodes 444 and 446 in a horizontal arrangement. As shown in this figure, EAP element region 448 may be disposed between EAP element regions 442 and 450. At least one of EAP element regions 442, 448, or 450 may include a voided or nanovoided electroactive polymer material. The other two EAP elements may be of similar or of disparate composition.

Figure 5:
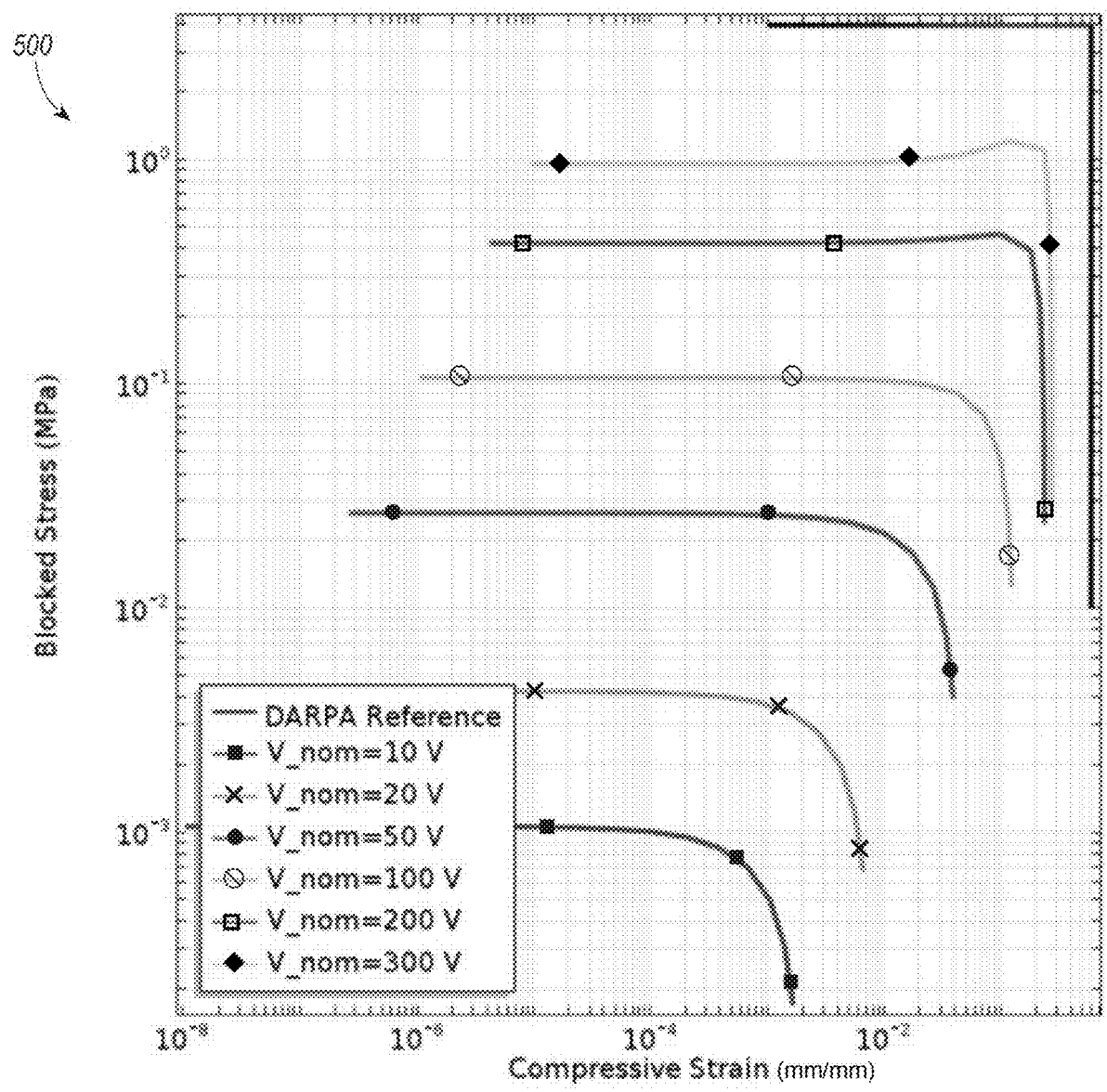
FIG. 5 is a graph showing blocked stress vs compressive strain for a range of voltages for an electroactive device in accordance with some embodiments.

FIG. 5 shows a numerically determined electroactive response of an electroactive device having a PDMS EAP element including nanovoided PDMS with 30% voids by volume. This EAP element had a thickness of 1 μm, where the sides used symmetric boundary conditions. A voltage was applied between two rigid electrodes, and the compressive strain (mm/mm) of the EAP element was measured as a function of blocked stress (MPa) for different voltages. The voids were assumed to be very small such that the PDMS properties were effectively homogeneous. The voids were filled with air at atmospheric pressure. The homogenous material model used is based on the properties of solid PDMS, the void fraction, and initial fill pressure. The material behavior is that of solid PDMS when the void fraction is zero. The results shown in FIG. 5 demonstrate that the higher voltages applied to the EAP material may increase the forces on the electrodes.

Figure 6:
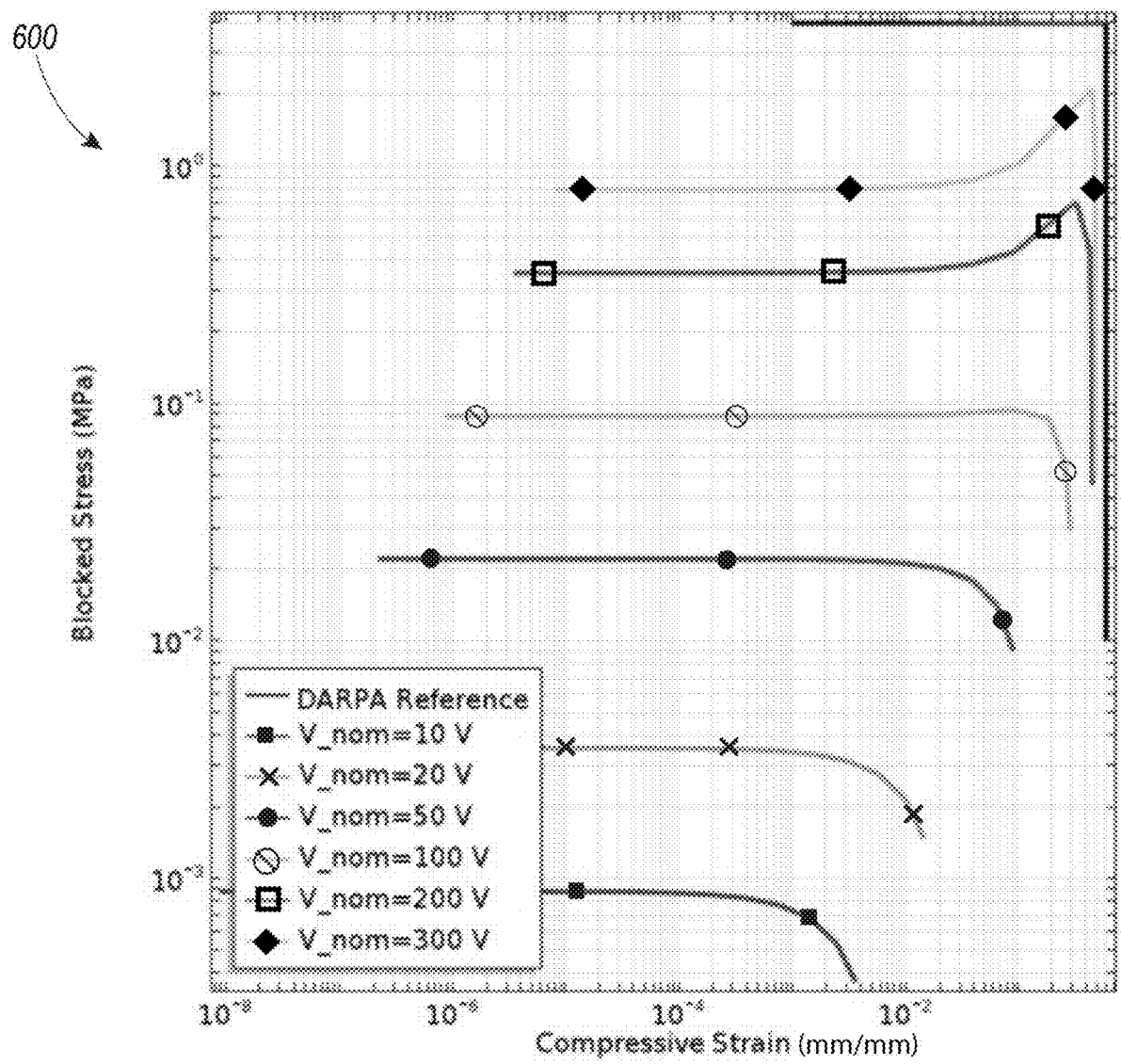
FIG. 6 is a graph showing blocked stress vs compressive strain for a range of voltages for an exemplary electroactive device in accordance with some embodiments.

FIG. 6 demonstrates the electroactive response of blocked stress (MPa) vs compressive strain (mm/mm) of an electroactive device having a PDMS EAP element including nanovoided PDMS with 50% voids by volume. The thickness of the PDMS EAP element was 1 μm. A voltage was applied between two rigid electrodes. As shown in FIG. 6, the increased presence of nanovoids by volume in the EAP element resulted in increased amounts of strain tolerable before the onset of saturation of the deformation, while lowering the induced stress. There was a distinct increase in achievable strain with reduced associated stress between the curves of the EAP element with 30% nanovoided polymer (FIG. 5) and those of the EAP element with 50% nanovoided polymer (FIG. 6). The increase in the strain is in the direction of the theoretical limit (DARPA reference).

Figure 7:
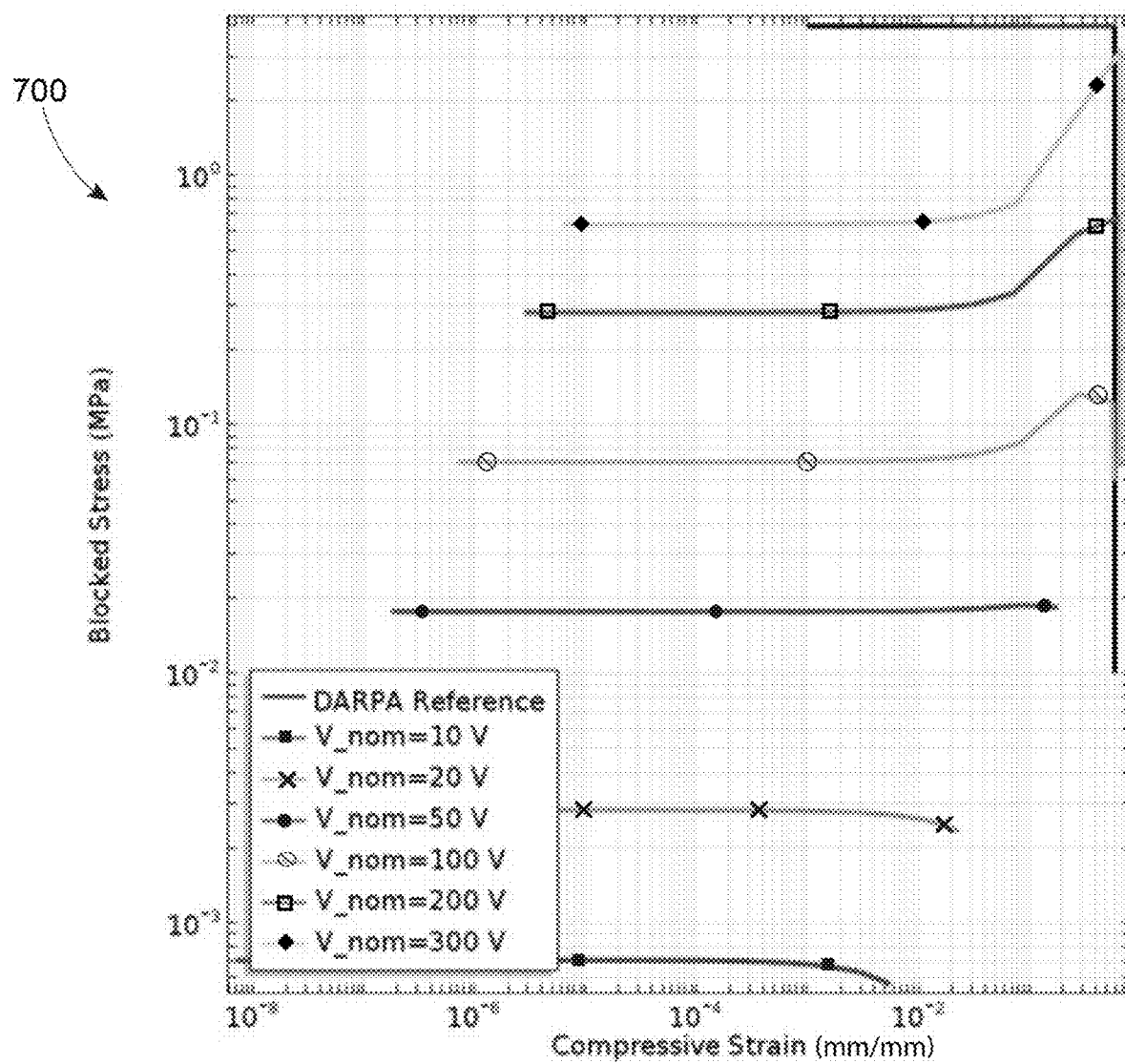
FIG. 7 is a graph showing blocked stress vs compressive strain for a range of voltages for an exemplary electroactive device in accordance with some embodiments.

FIG. 7 shows the electroactive response of blocked stress (MPa) vs compressive strain (mm/mm) of an electroactive device having a PDMS EAP element that included nanovoided PDMS with 70% voids by volume. The thickness of the PDMS EAP element was 1 μm. The increase in performance of the EAP element with 70% nanovoided polymer (FIG. 7) over the EAP elements having 30% and 50% nanovoided polymers (FIGS. 5 and 6) is even more evident than the increase between the comparative results of FIGS. 5 and 6.

From inspection of FIGS. 5-7, the following may be evident for the 300V nominal voltage numerically determined curves: that for strains less than 0.1, increasing the percentage of the content of nanovoids in the EAP material from 30% by volume to 70% by volume decreased the stress from about 1 to about 0.6 (MPa). Also, the limit before saturation of the deformation, represented by the strain, increased from about 0.2 to about 0.5 in the compressive strain (mm/mm) between the 30% and the 70% by volume nanovoid contributions, respectively. Each of these numerically determined curves approach the DARPA reference curve, with the increase in performance being due to the presence of the nanovoided EAP materials in the EAP elements of the tested electroactive devices.

Figure 8:
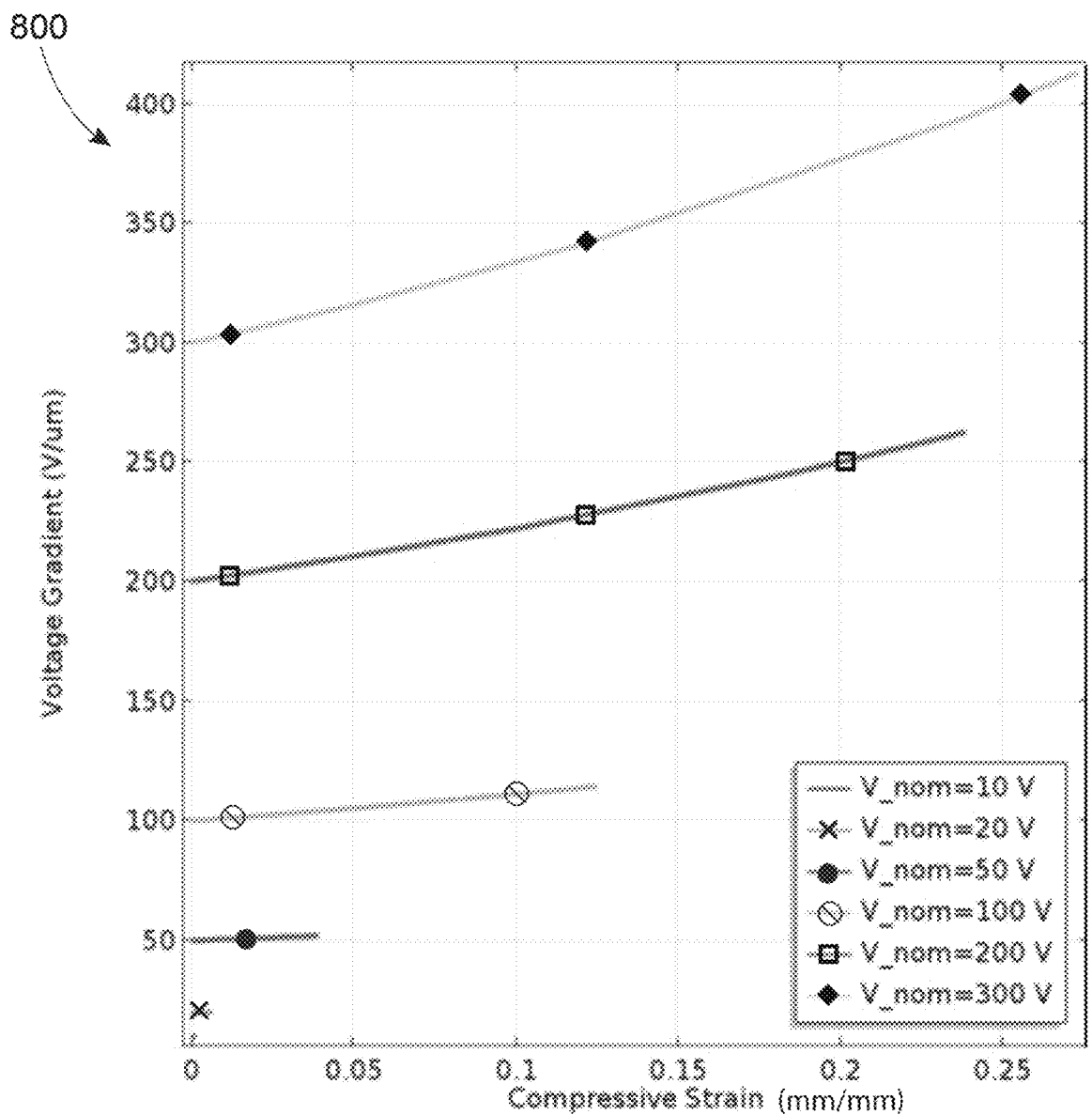
FIG. 8 is a graph showing voltage gradient vs compressive strain as a function of voltage for an exemplary electroactive device in accordance with some embodiments.

FIG. 8 shows the behavior of compressive strain (mm/mm) as a function of the voltage gradient (V/μm) for each of a set of potential differences for the device of FIG. 5 with a one μm thick PDMS EAP element and 30% voids by volume. At the nominal voltage of 300V, the achievable compressive strain is greater than about 0.25.

Figure 9:
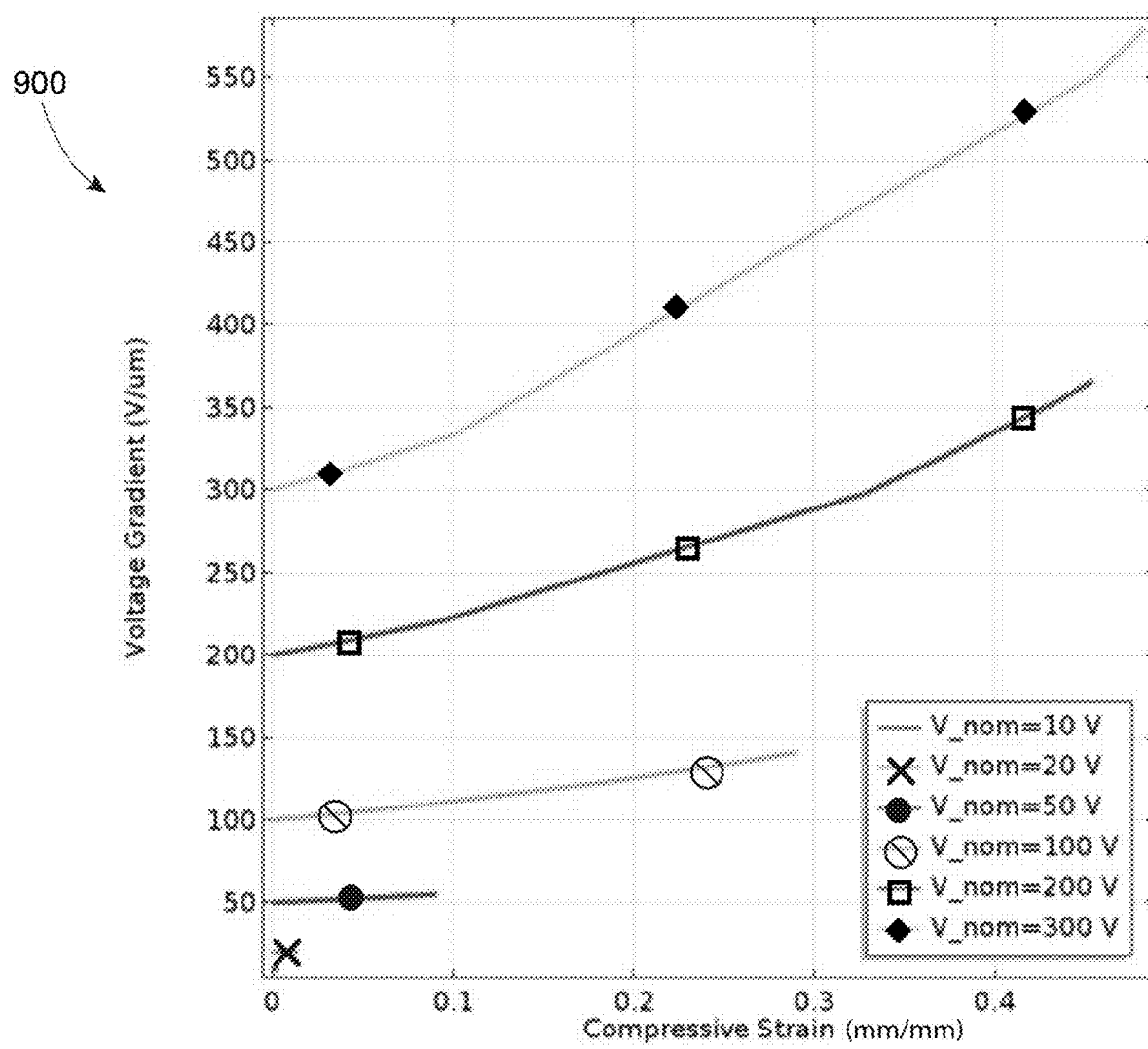
FIG. 9 is a graph showing voltage gradient vs compressive strain as a function of voltage for an exemplary electroactive device in accordance with some embodiments.

FIG. 9 shows the behavior of compressive strain (mm/mm) as a function of the voltage gradient (V/μm) for each of a set of potential differences for the device of FIG. 6 with a one μm thick PDMS EAP element and 50% voids by volume. At the nominal voltage of 300V, the achievable compressive strain is greater than about 0.4.

Figure 10:
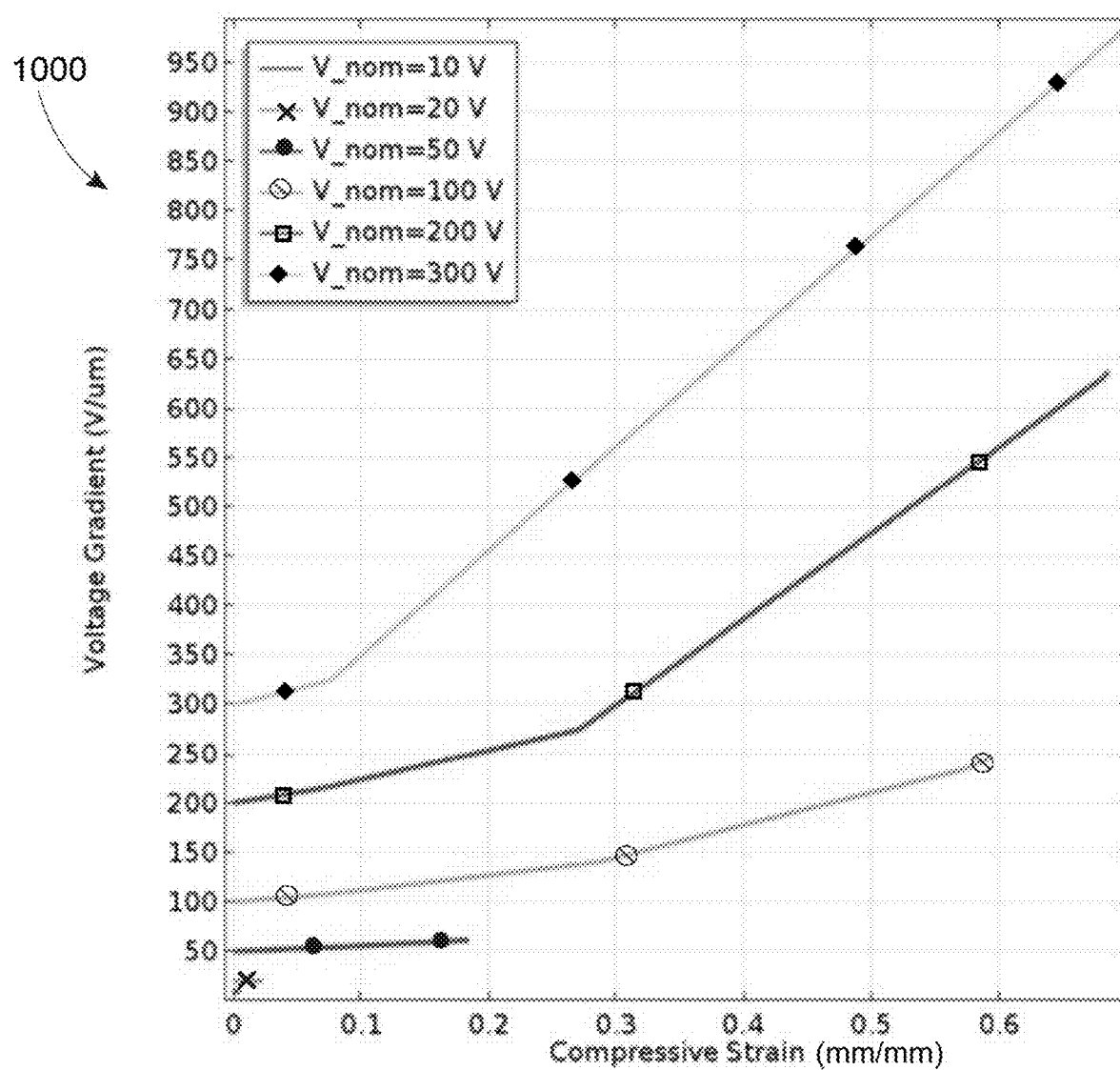
FIG. 10 is a graph showing voltage gradient vs compressive strain as a function of voltage for an exemplary electroactive device in accordance with some embodiments.

FIG. 10 shows the behavior of compressive strain (mm/mm) as a function of the voltage gradient for each of a set of potential differences for the device of FIG. 7 with a one μm thick PDMS EAP element and 70% voids. At the nominal voltage of 300V, the achievable strain is about 0.7. Moreover, the behavior of the device remains linear up until the last data point, yielding very high strains.

Each of FIGS. 8-10 present the voltage gradient (i.e., strength of the electrostatic field) as a function of compressive strain (mm/mm), for PDMS with 30%, 50%, and 70% nanovoids by volume. The result of a comparison reveals that increasing the nanovoid contribution in a PDMS EAP element, for example, increases the compressive strain achievable, while lowering the level of blocked stress (see FIGS. 5-7).

Figure 11:
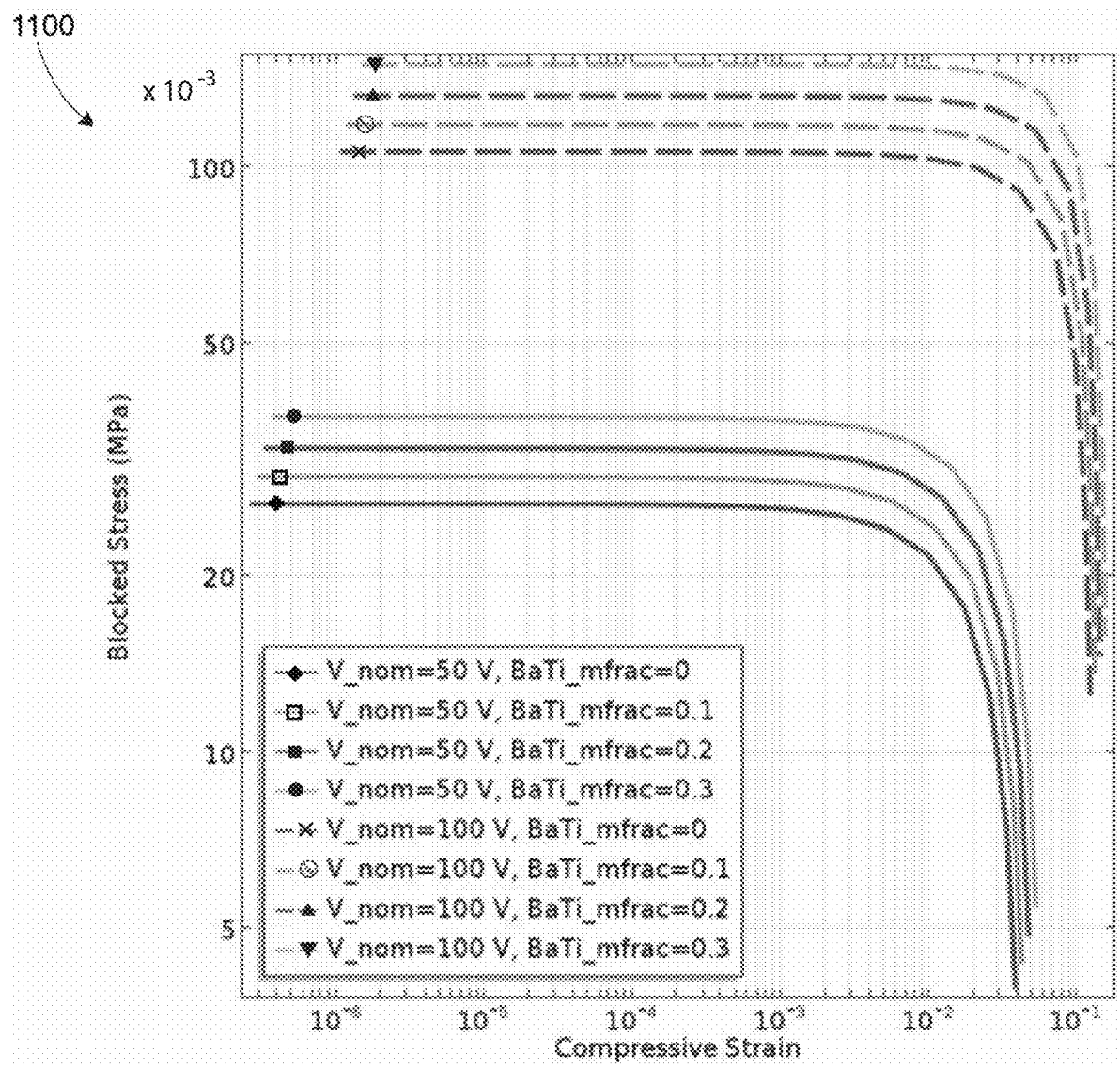
FIG. 11 is a graph showing the impact of incorporating barium titanate of various concentrations into an electroactive polymer element of an exemplary electroactive device structure in accordance with some of the embodiments.

In some embodiments, at least one component may be added to the EAP material of an EAP element to alter its electromagnetic properties. FIG. 11 shows the impact of incorporating barium titanate of various concentrations into a PDMS EAP polymer element in an electroactive device structure. For example, barium titanate ($BaTiO_3$), which is a member of the perovskite family and which may also include other titanates, and/or any other suitable component may be added to the EAP material. $BaTiO_3$ is a ferroelectric material with a relatively high dielectric constant (e.g., a value of between approximately 500 and approximately 7000) and polarization and may be used in various electroactive devices described herein. Besides large polarizability and permittivity, large strains may also be achievable with $BaTiO_3$. Pure $BaTiO_3$ is an insulator whereas upon doping it may transform into a semiconductor. The results shown in FIG. 11 demonstrate that the higher dielectric constants of the EAP materials (due to, for example, the addition of $BaTiO_3$) may increase the forces on the electrodes.

Figure 12:
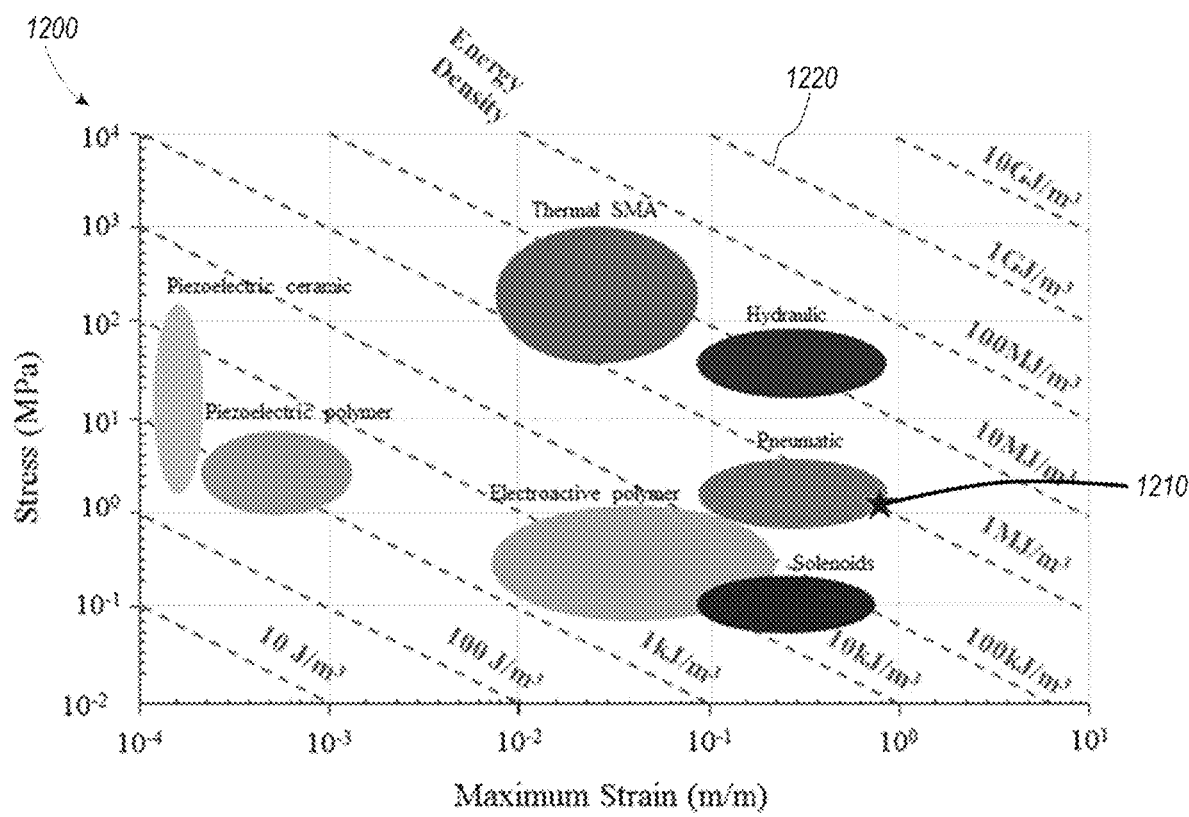
FIG. 12 is graph showing stress vs strain for a variety of actuator technologies.

FIG. 12 shows a graph 1200 illustrating the performance of a nanovoided polymer actuator relative to other existing practical solutions. Reference item 1210 represents the energy density (e.g., ergs/cm$^3$) for a 70% nanovoided PDMS. Its position in this graph demonstrates the efficacy of using nanovoids in polymers to increase the energy density relative to the use of polymers without any nanovoid contribution. Lines of constant energy density 1220 are indicated on the graph (the diagonally oriented dashed lines).

Figure 13:
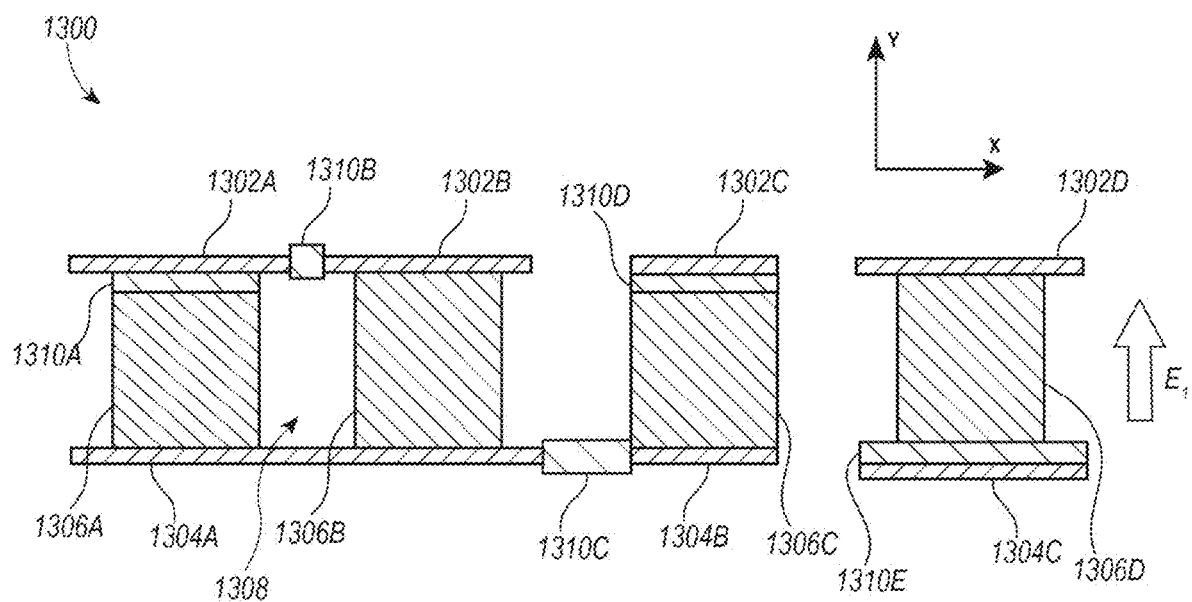
FIG. 13 shows cross-sectional views of exemplary arrangements of electroactive polymer elements in electroactive device structures in accordance with some embodiments.

FIG. 13 presents a cross-sectional schematic of an electroactive device 1300 including a plurality of EAP elements 1306A, 1306B, 1306C, and 1306D. Each of these EAP elements is disposed, respectively, between electrodes 1302A and 1304A, 1302B and 1304C, 1302C and 1304B, and 1302D and 1304C.

In accordance with some embodiments, electroactive device 1300 including EAP element 1306A disposed between electrodes 1302A and 1304A may additionally include a dielectric material 1310A disposed between electrode 1302A and EAP element 1306A. Dielectric material also may be disposed between adjacent electrodes. For example, as shown in FIG. 13, dielectric material 1310B may be disposed between electrodes 1302A and 1302B. These electrodes are associated with adjacent EAP elements 1306A and 1306B, respectively. Dielectric material 1310B may possess the same or a different dielectric constant than the other dielectric materials 1310A, 1310C, 1310D, and 1310E of electroactive device 1300. A similar arrangement is depicted in FIG. 13 between electrodes 1304A and 1304B, where dielectric 1310C material has been interposed therebetween. Dielectric material 1310C may possess the same or a different dielectric constant than the other dielectric materials 1310A, 1310B, 1310D, and 1310E of electroactive device 1300. The presence of a dielectric material in an electroactive device is further indicated in FIG. 13 where EAP element 1306C has paired electrodes 1302C and 1304B and dielectric material 1310D is disposed between electrode 1302C and EAP element 1306C. In some examples, EAP element 1306D may be separated from one of its electrodes 1304C by a dielectric material 1310E.

Two or more EAP elements of electroactive device 1300 may be separated from each other by a gap or interstitial volume. For example, as shown in FIG. 13, EAP elements 1306A and 1306B may be separated by an interstitial volume 1308. As shown in this figure, EAP elements 1306A and 1306B may share a common secondary electrode 1304A while not directly sharing a common primary electrode. According to some embodiments, electrodes 1302A, 1302B, 1302C, 1302D, 1304A, 1304B, and/or 1304C shown in FIG. 13 may include the same composition and/or electrical properties. In at least one example, electrodes 1302A, 1302B, 1302C, 1302D, 1304A, 1304B, and/or 1304C may vary in composition and/or may possess different electrical properties. Additionally or alternatively, dielectric materials 1310A, 1310B, 1310C, 1310D, and/or 1310E may include the same composition and/or electrical properties. According to some embodiments, dielectric materials 1310A, 1310B, 1310C, 1310D, and/or 1310E may vary in composition and/or electrical properties. In some embodiments, EAP elements 1306A, 1306B, 1306C, and/or 1306D may include the same composition and/or electrical properties. According to at least one embodiment, EAP elements 1306A, 1306B, 1306C, and/or 1306D may vary in composition and/or may possess different electromechanical responses to the same electrostatic field strength. According to some embodiments, paired electrodes 1302A/1304A, 1302B/1304A, 1302C/1304B, and/or 1302D/1304C may provide the same or different electrostatic field strengths at various times. Additional or alternative electrode and/or EAP element configurations may be utilized in electroactive devices in various embodiments.

Figure 16:
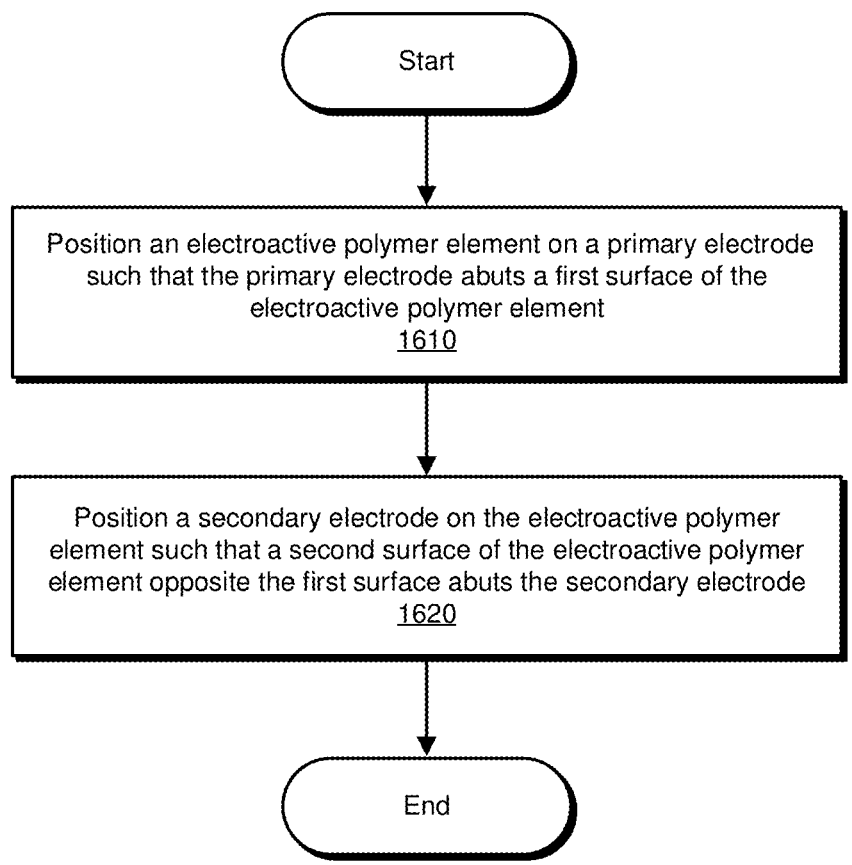
FIG. 16 is a flow chart depicting a method of manufacturing an electroactive device in accordance with some of the embodiments.

Electroactive devices (e.g., electroactive actuators) as described herein may include at least two paired electrodes (e.g., opposing electrodes respectively specified as a primary electrode and a secondary electrode). When each of the primary electrodes and each of the secondary electrodes are separately energized with a different potential, an electrostatic field may be produced between each of the primary and secondary electrode pairs. Additionally or alternatively, there may be a pairing of a plurality of primary electrodes with a single common secondary electrode or vice versa (see, e.g., FIG. 13 showing electrodes 1302A and 1302B with common electrode 1304A). For a given electroactive device, either or both of the primary and secondary electrodes may partially or entirely cover the first or second surfaces (i.e., common areal overlap) of the associated EAP elements (see, e.g., FIG. 13 showing electroactive device 1300 with electrodes 1302C and 1304B abutting first and second surfaces of EAP element 1306C). While the geometric depiction of EAP elements 1306A-D in FIG. 16 is of rectangular form, EAP elements may include any suitable quadrilateral and/or other geometric forms.

According to some embodiments, a set of primary electrodes may have a first subset of electrodes with each member of that subset at a common first potential. A set of secondary electrodes may have a second subset of electrodes with each member of that subset at a common second potential. At least one electrode from the first subset may be paired with at least one electrode from the second subset. In some embodiments, at least one of a primary electrode or a secondary electrode may be movable such that the electrode is movable in conjunction with displacement of an abutting surface portion of the EAP element. According to at least one embodiment, one of the primary or secondary electrodes may be a movable electrode and the other electrode may be a fixed electrode that holds an abutting or corresponding surface portion of the EAP element in a fixed position.

In some embodiments, an electroactive device may include a stack having a plurality of layers (e.g., five or more layers) with two or more layered EAP elements. For example, the electroactive device may include a stack of electrodes, EAP elements, and, optionally, dielectric layers. Such an electroactive device may, for example, include (1) a primary electrode connected to a first voltage, (2) at least one of a first set of EAP elements, (3) a secondary electrode connected to a second voltage, (4) at least one of a second set of EAP polymers, and (5) a tertiary electrode connected to a third voltage. The first and third voltages may be the same or different.

Figure 14:
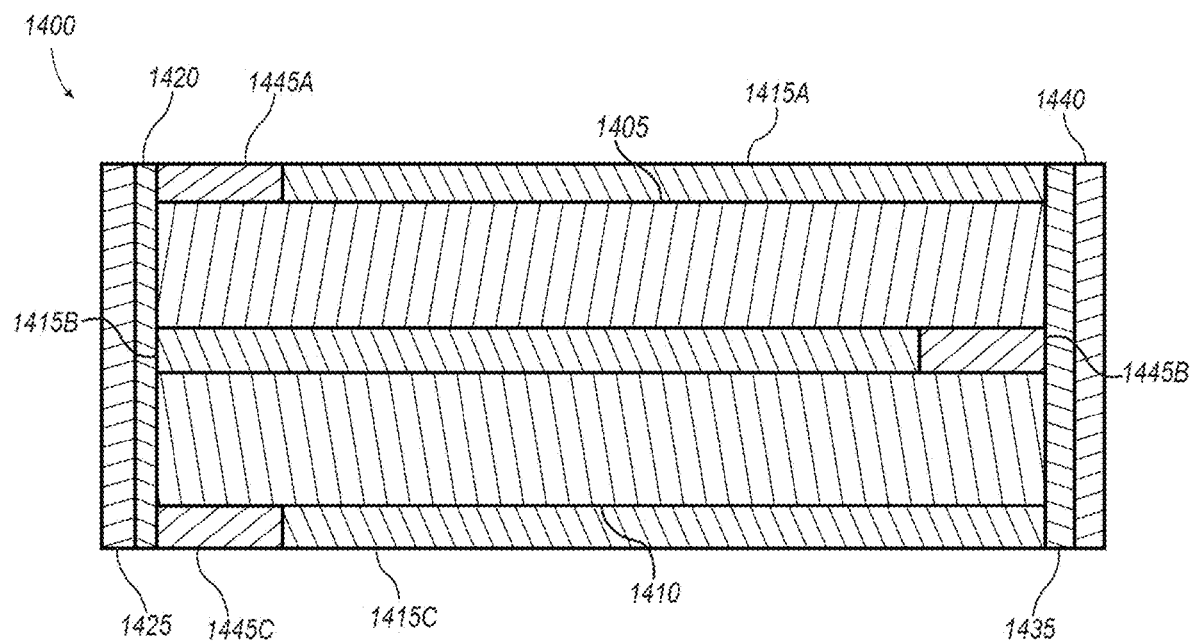
FIG. 14 shows a cross-sectional view of a multilayer electroactive device in accordance with some of the embodiments.

FIG. 14 shows an exemplary electroactive device 1400 having a plurality of layers arranged as a stack, the plurality of layers including a first EAP element 1405 disposed between a primary electrode 1415A and a secondary electrode 1415B, and second EAP element 1410 disposed between secondary electrode 1415B and a tertiary electrode 1415C. First EAP element 1405 and second EAP element 1410 may each include any suitable material, such as, for example, a nanovoided EAP material as described herein. Electrical connections to primary electrode 1415A, secondary electrode 1415B, and tertiary electrode 1415C may be provided in any suitable manner. For example, such electrical connections may be provided by side conductors distributed along the side of the stack, as they are depicted in FIG. 14, where secondary electrode 1415B is connected via a first schoopage layer 1420 to a first common electrode 1425. Additionally, as shown in this figure, primary electrode 1415A and secondary electrode 1415C may be connected via a second schoopage layer 1435 to a second common electrode 1440. Primary electrode 1415A, secondary electrode 1415B, and/or tertiary electrode 1415C may be semi-isolated or isolated from each other by dielectric materials (e.g., an insulator layers), such as dielectric materials 1445A, 1445B, and 1445C shown in FIG. 14.

In some embodiments, first schoopage layer 1420, first common electrode 1425, second schoopage layer 1435, and/or second common electrode 1440 may be structured in a number of different ways than that shown in FIG. 14. For example, first common electrode 1425 and/or second common electrode 1440 may include of a number of electrically conductive fingers, each electrically isolated from one another, descending from the top of electroactive device 1400, ascending from below electroactive device 1400, and/or originating from the side and proceeding parallel to the top or bottom of the electrode. In some embodiments, first common electrode 1425 and/or second common electrode 1440 may have a more complex or flexible shape to allow compression and/or expansion during deformation. First and second common electrodes 1425 and 1440 may possess any suitable shape and configuration so as to electrically engage primary electrode 1415A, secondary electrode 1415B, and tertiary electrode 1415C, respectively.

In some embodiments, primary electrode 1415A, secondary electrode 1415B, tertiary electrode 1415C, first schoopage layer 1420, first common electrode 1425, second schoopage layer 1435, and/or second common electrode 1440 may be self-healing such that damage from local shorting of a circuit can be isolated. Suitable self-healing electrodes may include thin films of metal, such as for example, aluminum having a thickness of approximately 30 nm (e.g., a thickness of from approximately 5 nm to approximately 50 nm). Appropriate electrode materials additionally or alternatively may include indium, gallium, zinc, and/or any other suitable metal or combination of metals. Other suitable conductive electrode materials may include, for example, carbon nanotubes, graphene, transparent conductive oxides, and/or any other suitable electrically conductive material. In some embodiments, primary electrode 1415A, secondary electrode 1415B, and/or tertiary electrode 1415C may be separated from first EAP element 1405 and/or second EAP element 1410 by a dielectric material such as a dielectric coating as described above.

According to various embodiments, an electroactive device may include a series of electrode pairs each having an EAP element disposed therebetween. Characteristics of the layered EAP elements may be the same and/or may vary between layers, such characteristics including, for example, effective dielectric constants, size distributions of nanovoid cells, closed- and/or open-celled nanovoids, percentages of nanovoids (e.g., nanovoid content by volume), and/or EAP element thicknesses. In at least one embodiment, adjacent electrodes that are separated by an EAP element, and optionally at least one dielectric layer, may be supplied with different potentials, resulting in deformation of the respective EAP elements interposed between the adjacent electrodes.

According to at least one embodiment, an electroactive device may include a stack of N EAP elements layered with N+1 electrodes (see, e.g., FIG. 14). In some examples, an electroactive device may include a stack of N EAP elements layered with 2N electrodes, with N−1 dielectric layers optionally disposed between adjacent electrodes that are not separated from each other by EAP elements. For example, as depicted in FIG. 15, a basic electroactive unit may be replicated as desired in an electroactive device having N electroactive units (i.e., an N-stack), with additional layers, such as interposed dielectrics layers, disposed between adjacent electroactive units in the electroactive device.

Figure 15:
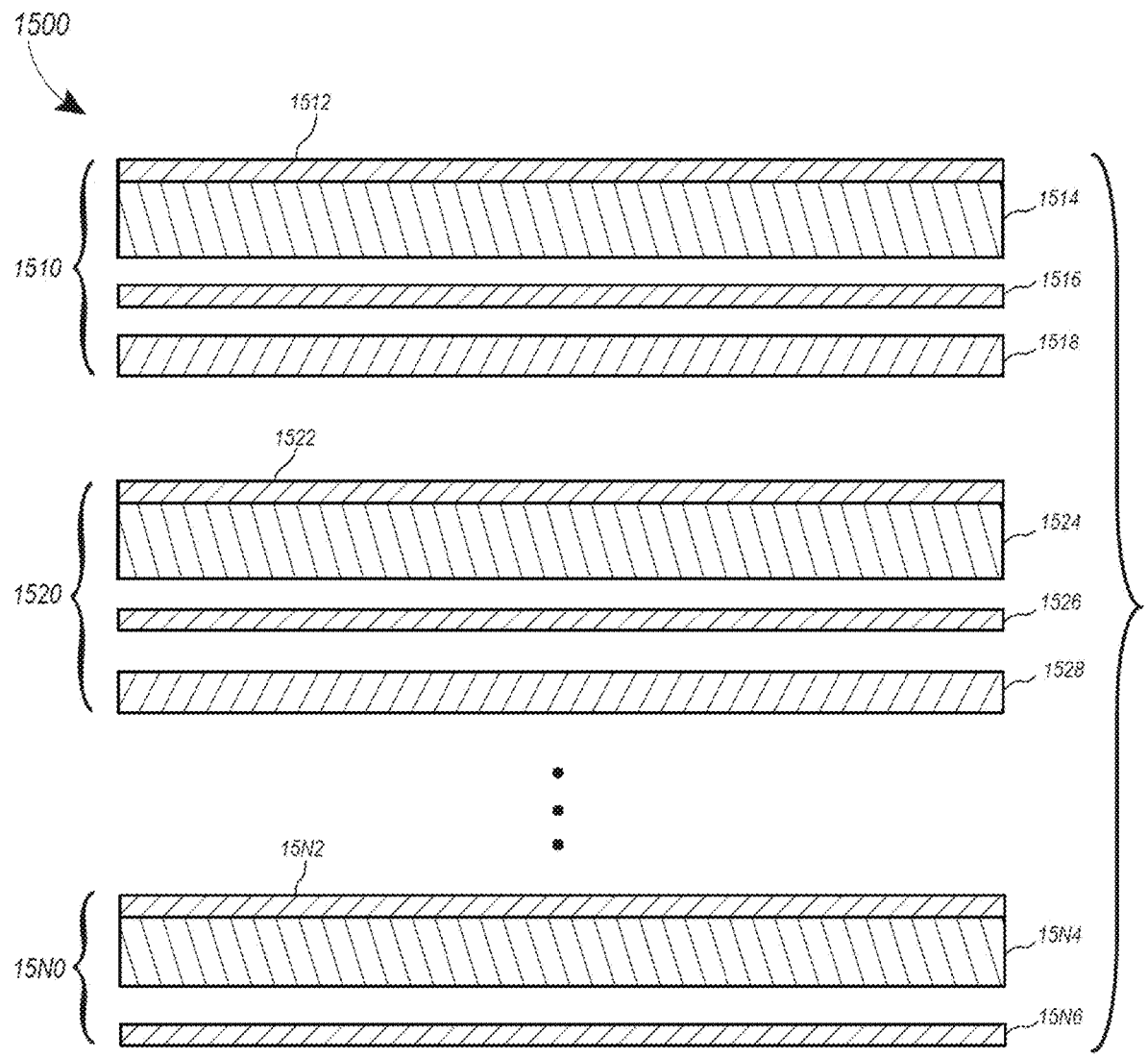
FIG. 15 shows a cross-sectional view of a multilayer electroactive device in accordance with some of the embodiments.

In some embodiments, as shown in FIG. 15, a basic electroactive unit 1510 may include at least one electrode, such as electrode 1512, layered with at least one EAP element, such as EAP element 1514. EAP element 1514 may include one or more electroactive polymer layers, in which at least one of these polymer layers may include a nanovoided electroactive polymer material and/or any other suitable electroactive material in accordance with any of the embodiments described herein. According to some embodiments, a second electrode 1516 may be included in electroactive unit 1510. In this example, a dielectric layer, such as dielectric material 1518, may be disposed between electrode 1516 and an electrode 1522 of an adjacent basic electroactive unit 1520. Thus, there may be variations on how the individual basic units that include the N-stack are assembled.

Electroactive device 1500 may include multiple electroactive units as shown in FIG. 15. For example, electroactive device 1500 may include electroactive unit 1510, as described above, and adjacent electroactive unit 1520, which includes, for example, electrode 1522, layered with at least one EAP element, such as EAP element 1524. In some examples, electroactive unit 1520 may also include an electrode 1526, with EAP element 1524 disposed between electrode 1522 and electrode 1526. In this example, electroactive unit 1520 may include a dielectric material 1528 disposed between electrode 1526 and an electrode of a subsequently stacked electroactive unit. Electroactive device 1500 may include suitable number of electroactive units, without limitation. For example, electroactive device 1500 may include a stack of from two electroactive units to thousands of electroactive units (e.g., from 2 electroactive units to approximately 5, approximately 10, approximately 20, approximately 30, approximately 40, approximately 50, approximately 100, approximately 200, approximately 300, approximately 400, approximately 500, approximately 600, approximately 700, approximately 800, approximately 900, approximately 1000, approximately 2000, greater than approximately 2000 electroactive units). As shown in FIG. 15, N may represent the total number of stacked electroactive units, with electroactive unit 15N0 being located furthest from electroactive unit 1510.

In some embodiments, a basic electroactive unit may have one electrode (e.g., electrode 1512) and one electroactive polymer layer (e.g., EAP element 1514) that is disposed against an electrode (e.g., electrode 1522) of an adjacent electroactive unit (e.g., electroactive unit 1520). The final Nth-basic unit (e.g., 15N0) may include an electrode 15N2, an EAP element 15N4, and may be completed by the addition of an Nth+1 electrode 15N6. Electroactive device 1500 may contain at least one nanovoided EAP element. Additionally or alternatively, a basic electroactive unit may include two electrodes (e.g., electrodes 1512 and 1516 as shown in FIG. 15). In at least one example, a basic electroactive unit may include a plurality of polymer layers, one or more dielectric layers, and/or any combination thereof. The various electrodes 1512, 1516 (if present), 1522, 1526 (if present), . . . , 15N22 and 15N6 may possess varying electrical properties. The various EAP elements 1514, 1524, . . . 15N4 each may include the same or different electroactive polymer materials and/or combination of electroactive polymer materials, some of which may possess differing dopants, permittivities, thicknesses, nanovoid contributions, and/or other characteristics.

Nanovoided materials, such as nanovoided polymer materials of EAP elements as described herein, may include any suitable polymers, without limitation. Examples of suitable nanovoided polymer materials may include acrylates, halogenated polymers, such as PVDF and/or copolymers of PVDF, including PVDF-TrFE, silicones, such as PDMS, acrylates, styrenes, polyesters, polycarbonates, epoxies, and/or other suitable polymeric material. In some examples, the nanovoided polymer materials may include any suitable nanoparticles to increase the dielectric constant of the polymer materials, including, for example, barium titanate (BaTiO$_3$), TiO$_2$, CeO$_2$, BaSrTiO$_3$, PbLaZrTiO$_3$, PbMgNbO$_3$+PbTiO$_3$, Ta$_2$O$_3$, and/or Al$_2$O$_3$O$_3$.

Nanovoided materials, such as nanovoided polymer materials of EAP elements as described herein, may be formed using any suitable techniques. In at least one embodiment, a nanovoided polymer material may be formed by mixing a curable material with one or more solvents. The curable material may include any suitable curable compound and/or combination of curable compounds, such as a curable resin mixture and/or other curable mixture, that includes one or more monomers, oligomers, and/or prepolymers. In some embodiments, the curable material may include a mixture of curable monomers, oligomers, and/or prepolymers combined with cured polymers. The curable material may be cured in any suitable manner, such as by a chain-reaction or a step-reaction.

The curable material used to form the nanovoided polymer material may include any suitable material, such as, for example, an acrylate with a free radical initiator (e.g., a thermal initiator and/or an ultraviolet (UV) initiator). The cured polymer may include any suitable polymer material, including, for example, a silicone-based polymer that is cured with a hydrosilylation catalyst (e.g., a UV and/or thermally initiated hydrosilylation catalyst, such as Bis(acetylacetonate)platinum II and/or n(2-cyclopentadienyl) trialkylplatinum). In some examples, a chain-reaction polymerized system may include a curable material that is cured by exposure to an elevated temperature, UV radiation, and/or other actinic radiation (e.g., x-rays, extreme UV radiation, electron beams, etc.). In at least one example, the curable material may be cured by exposure to carbon compounds, such as graphene. Additionally or alternatively, the curing process may be initiated by, for example, remotely forming a free-radical initiator, which is then brought into contact with the curable material. The layer of curable material and/or one at least one of the first conductive layer and the second conductive layer may deposited on a surface, such as an electrode surface, in any suitable manner, including, for example, by printing (e.g., inkjet printing, silkscreen printing, etc.).

The one or more solvents mixed with the curable material may be highly miscible with monomers, oligomers, and/or prepolymers in the curable material and may be immiscible with the resulting cured polymer material such that nanovoids including the solvent are formed in the polymer material during curing. In at least one example, two or more solvents may be used to modify the solubility parameter of the solvent. Additionally or alternatively, a mixture having multiple solvents may include a first solvent with a high vapor pressure that dries more quickly on formation of a coating and a second solvent that dries more slowly after curing. In some embodiments, the curable material and solvent may additionally be mixed with one or more initiators to facilitate curing and/or one or more nanofillers to increase the dielectric constant of the resulting cured polymer material. In at least one example, the one or more solvents may be removed from the nanovoids formed in the polymer material during and/or following curing such that the nanovoids are filled with gas, such as air and/or any other suitable gas or mixture of gasses in the cured polymer material. In some examples, the one or more solvents may be evaporated and may pass through the polymer material.

In at least one example, a nanovoided polymer material may be formed by mixing a curable material with one or more cavitation agents. Examples of cavitation agents include, without limitation, beta-keto acetic acids, such as acetone dicarboxylic acid, and/or any other suitable cavitation agent. Such a cavitation agent may include any suitable component that readily decomposes under curing conditions (e.g., elevated heat, light, radiation, etc.) to form nanovoids that include decomposition products of the cavitation agent within the polymer material during curing. The one or more cavitation agents may be included in a curable mixture with or without at least one solvent. In at least one example, the decomposition products may be removed from the nanovoids formed in the polymer material during and/or following curing such that the nanovoids are filled with gas, such as air and/or any other suitable gas or mixture of gasses in the cured polymer material.

An exemplary method 1600 of manufacturing an electroactive device, such as an electroactive actuator, is shown in FIG. 16. As shown in FIG. 16, at step 1610, an electroactive polymer element may be positioned on a primary electrode such that the primary electrode abuts a first surface of the electroactive polymer element. In at least one example, the electroactive polymer element may include a nanovoided polymer material. For example, EAP element 306 may be positioned on primary electrode 302 such that the primary electrode 302 abuts first surface 308 of EAP element 306 (see FIGS. 3A and 3B; see also FIGS. 1, 4A-4C, and 13-15).

At step 1620, a secondary electrode may be positioned on the electroactive polymer element such that a second surface of the electroactive polymer element opposite the first surface abuts the secondary electrode. For example, secondary electrode 304 may be positioned on EAP element 306 such that second surface 310 of EAP element 306 abuts secondary electrode 304. EAP element 306 may be deformable from an initial state to a deformed state when a voltage is applied between primary electrode 302 and secondary electrode 304 (see FIGS. 3A and 3B).

Figure 17:
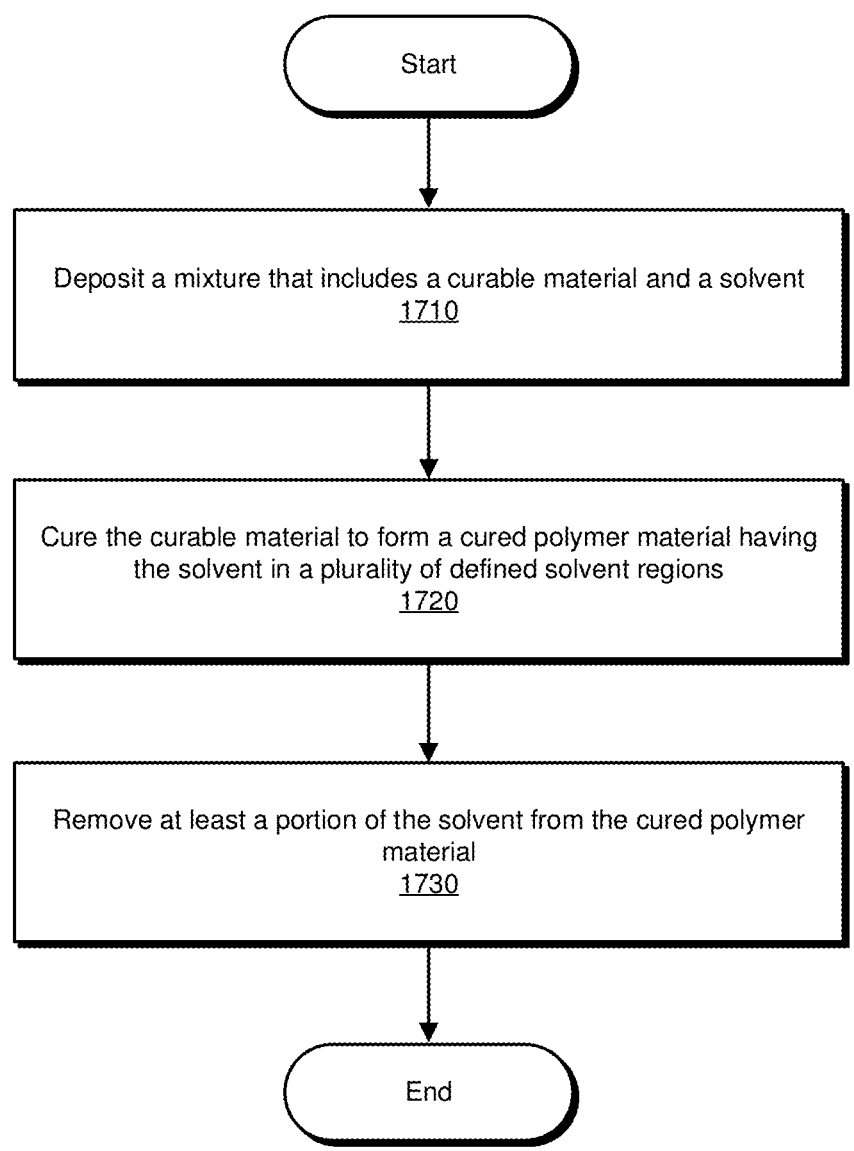
FIG. 17 is a flow chart depicting a method of manufacturing a nanovoided polymer material in accordance with some of the embodiments.

An exemplary method 1700 of forming an electroactive polymer element (e.g., EAP element 306) that includes a nanovoided polymer material, such as an electroactive polymer element of an electroactive device, is shown in FIG. 17. According to some embodiments, as shown in FIG. 17, at step 1710, a mixture that includes a curable material and a solvent may be deposited. For example, a mixture that includes a curable material and a solvent may be deposited on primary electrode 302 (e.g., by spin coating and/or inkjet deposition).

At step 1720, the curable material may be cured to form a cured polymer material having the solvent in a plurality of defined solvent regions. For example, the curable material may be cured by exposure to actinic radiation (e.g., UV radiation, etc.), elevated temperature, a polymerization initiator (e.g., a free-radical initiator, graphene, etc.), and/or any other suitable curing medium to form a cured polymer material having the solvent in a plurality of defined solvent regions.

At step 1730, at least a portion of the solvent may be removed from the cured polymer material. For example, at least a portion of the solvent may be evaporated and removed during or following curing of the polymer material. In at least one example, removing at least the portion of the solvent from the cured polymer material may form a plurality of voids in the resulting nanovoided polymer material.

Figure 18:
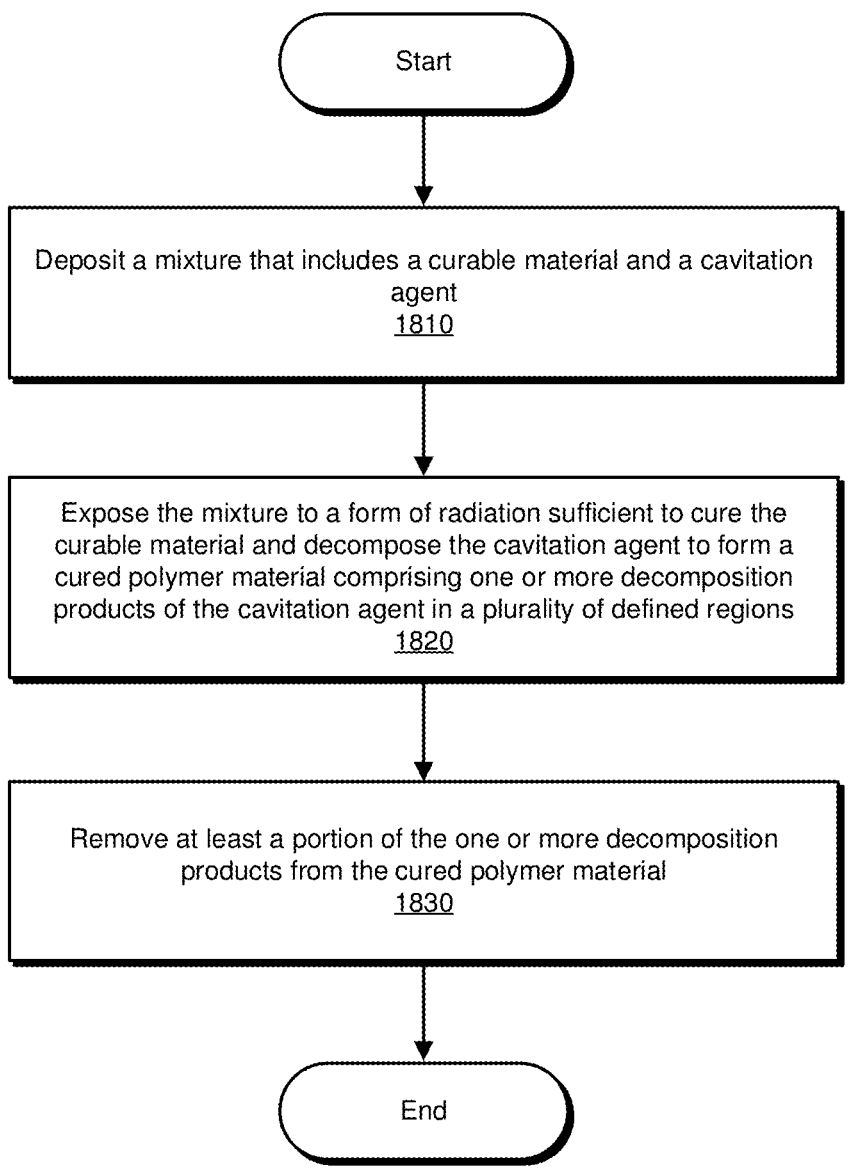
FIG. 18 is a flow chart depicting a method of manufacturing a nanovoided polymer material in accordance with some of the embodiments.

An exemplary method 1800 of forming an electroactive polymer element (e.g., EAP element 306) that includes a nanovoided polymer material, such as an electroactive polymer element of an electroactive device, is shown in FIG. 18. In at least one embodiment, as shown in FIG. 18, at step 1810, a mixture comprising a curable material and a cavitation agent may be deposited. For example, a mixture that includes a curable material and a cavitation agent (e.g., a beta-keto acetic acid) may be deposited on primary electrode 302. In some examples, the mixture may also include a solvent and the cured polymer material may further include the solvent in a plurality of defined regions.

At step 1820, the mixture may be exposed to a form of radiation sufficient to cure the curable material and decompose the cavitation agent to form a cured polymer material comprising one or more decomposition products of the cavitation agent in a plurality of defined regions. At step 1830, at least a portion of the one or more decomposition products may be removed from the cured polymer material.

As discussed throughout the instant disclosure, the disclosed devices, systems, and methods may provide one or more advantages over conventional devices. For example, in contrast to prior devices, electroactive devices presented herein may include EAP elements that achieve substantially uniform strain in the presence of an electrostatic field produced by a potential difference between paired electrodes, permitting the electroactive devices to achieve, for example, improvements in both energy density and specific power density. Such uniform strain may reduce or eliminate unwanted deformations in the EAP elements and may result in greater overall deformation, such as compression, of the EAP elements, providing a greater degree of movement of surface regions of the EAP elements while requiring a lower amount of energy to provide such deformation. The EAP elements may include polymer materials having nanovoided regions that allow for additional compression in the presence of a voltage gradient in comparison to non-voided materials. Additionally, an electroactive device may be formed in a stacked structure having a plurality of EAP elements that are layered with multiple electrodes, enabling the plurality of EAP elements to be actuated in conjunction with each other in a single device that may undergo a more substantial degree of deformation (e.g., compression and/or expansion) in comparison to an electroactive device having a single EAP element or layer.

Electroactive devices described and shown herein may be utilized in any suitable technologies, without limitation. For example, such electroactive devices may be utilized as mechanical actuators to actuate movement of adjacent components. In at least one embodiment, the disclosed electroactive devices may be incorporated into optical systems such as adjustable lenses (e.g., fluid-filled lenses) to actuate movement of one or more optical layers. Such actuation may, for example, allow for selected movement of lens layers of an adjustable lens, resulting in deformation of the lens layers to adjust optical characteristics (e.g., focal point, spherical correction, cylindrical correction, axial correction, etc.) of the adjustable lens. In some embodiments, electroactive devices as disclosed herein may be utilized as actuators in micromechanical apparatuses, such as microelectromechanical devices. Additionally or alternatively, electroactive devices may be used for converting mechanical energy to electrical energy for use in energy harvesting systems and/or sensor apparatuses.

Embodiments of the instant disclosure may include or be implemented in conjunction with an artificial reality system. Artificial reality is a form of reality that has been adjusted in some manner before presentation to a user, which may include, e.g., a virtual reality (VR), an augmented reality (AR), a mixed reality (MR), a hybrid reality, or some combination and/or derivatives thereof. Artificial reality content may include completely generated content or generated content combined with captured (e.g., real-world) content. The artificial reality content may include video, audio, haptic feedback, or some combination thereof, any of which may be presented in a single channel or in multiple channels (such as stereo video that produces a three-dimensional effect to the viewer). Additionally, in some embodiments, artificial reality may also be associated with applications, products, accessories, services, or some combination thereof, that are used to, e.g., create content in an artificial reality and/or are otherwise used in (e.g., perform activities in) an artificial reality. The artificial reality system that provides the artificial reality content may be implemented on various platforms, including a head-mounted display (HMD) connected to a host computer system, a standalone HMD, a mobile device or computing system, or any other hardware platform capable of providing artificial reality content to one or more viewers.

The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

The preceding description has been provided to enable others skilled in the art to best utilize various aspects of the exemplary embodiments disclosed herein. This exemplary description is not intended to be exhaustive or to be limited to any precise form disclosed. Many modifications and variations are possible without departing from the spirit and scope of the instant disclosure. The embodiments disclosed herein should be considered in all respects illustrative and not restrictive. Reference should be made to the appended claims and their equivalents in determining the scope of the instant disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising."

What is claimed is:

1. An electroactive device comprising:
   an electroactive polymer element having a first surface and a second surface opposite the first surface, the electroactive polymer element comprising a nanovoided polymer material;
   a primary electrode abutting the first surface of the electroactive polymer element; and
   a secondary electrode abutting the second surface of the electroactive polymer element;
   wherein:
   the electroactive polymer element is deformable from an initial state to a deformed state by application of an electrostatic field produced by a potential difference between the primary electrode and the secondary electrode;

the electroactive polymer element has a maximum thickness of from 100 nm to 10 μm in an undeformed state; and each of the primary electrode and the secondary electrode has a thickness of from 10 nm to 1 μm.

2. The electroactive device of claim 1, wherein the deformed state of the electroactive polymer element comprises a compressed state.

3. The electroactive device of claim 1, wherein the nanovoided polymer material defines a plurality of voids having diameters of from 10 nm to 1 μm.

4. The electroactive device of claim 1, wherein the nanovoided polymer material defines a plurality of voids collectively occupying from 10% by volume to 90% by volume of the nanovoided polymer material when the electroactive polymer element is in an undeformed state.

5. The electroactive device of claim 1, wherein the nanovoided polymer material comprises a polymer having an elastic modulus of 10 GPa or less.

6. An electroactive device comprising:
a primary electrode;
a secondary electrode overlapping the primary electrode;
a tertiary electrode overlapping the primary electrode and the secondary electrode;
a first electroactive polymer element disposed between and abutting the primary electrode and the secondary electrode, the first electroactive polymer element comprising a nanovoided polymer material; and
a second electroactive polymer element disposed between and abutting the secondary electrode and the tertiary electrode, the second electroactive polymer element comprising a nanovoided polymer material;
wherein:
the first electroactive polymer element is deformable from an initial state to a deformed state when a first electrostatic field is generated between the primary electrode and the secondary electrode; and
the second electroactive polymer element is deformable, in conjunction with deformation of the first electroactive polymer element, from an initial state to a deformed state when a second electrostatic field is generated between the secondary electrode and the tertiary electrode;
the first electroactive polymer element has a maximum thickness of from 100 nm to 10 μm in an undeformed state; and
each of the primary electrode and the secondary electrode has a thickness of from 10 nm to 1 μm.

7. The electroactive device of claim 6, wherein the first electrostatic field is equal to the second electrostatic field.

8. A method for forming an electroactive device comprising:
positioning an electroactive polymer element on a primary electrode such that the primary electrode abuts a first surface of the electroactive polymer element, the electroactive polymer element comprising a nanovoided polymer material; and
positioning a secondary electrode on the electroactive polymer element such that a second surface of the electroactive polymer element opposite the first surface abuts the secondary electrode;
wherein:
the electroactive polymer element is deformable from an initial state to a deformed state when a voltage difference of at least a certain value is applied between the primary electrode and the secondary electrode;
the electroactive polymer element has a maximum thickness of from 100 nm to 10 μm in an undeformed state; and
each of the primary electrode and the secondary electrode has a thickness of from 10 nm to 1 μm.

9. The method of claim 8, further comprising forming the electroactive polymer element comprising the nanovoided polymer material by:
depositing a mixture comprising a curable material and a cavitation agent;
exposing the mixture to a form of radiation sufficient to cure the curable material and decompose the cavitation agent to form a cured polymer material comprising one or more decomposition products of the cavitation agent in a plurality of defined regions; and
removing at least a portion of the one or more decomposition products from the cured polymer material.

10. The method of claim 9, wherein the cavitation agent comprises a beta-keto acetic acid.

11. The method of claim 9, wherein:
the mixture further comprises a solvent; and
the cured polymer material further comprises the solvent in the plurality of defined regions.

12. The method of claim 8, further comprising forming the electroactive polymer element comprising the nanovoided polymer material by:
depositing a mixture comprising a curable material and a solvent;
curing the curable material to form a cured polymer material comprising the solvent in a plurality of defined solvent regions; and
removing at least a portion of the solvent from the cured polymer material.

13. The method of claim 12, wherein removing at least the portion of the solvent from the cured polymer material forms a plurality of voids resulting in the nanovoided polymer material.

14. The method of claim 12, wherein the curable material comprises an acrylate material and the mixture further comprises a free radical initiator of at least one of a thermal initiator or an ultraviolet initiator.

15. The method of claim 12, wherein the cured polymer material comprises poly(dimethylsiloxane).

16. The method of claim 12, wherein depositing the mixture comprising the curable material and the solvent further comprises depositing the mixture on the primary electrode.

17. The method of claim 12, wherein depositing the mixture comprising the curable material and the solvent further comprises depositing the mixture by at least one of spin coating or inkjet deposition.

18. The method of claim 12, wherein the cured polymer material comprises a silicone-based polymer material.

19. The method of claim 18, wherein the mixture further comprises a hydrosilylation catalyst.

* * * * *